United States Patent
Yen et al.

(10) Patent No.: US 9,029,089 B2
(45) Date of Patent: May 12, 2015

(54) METHODS FOR PREDICTING SURVIVAL IN CANCER PATIENTS

(75) Inventors: Yun Yen, Arcadia, CA (US); Qiang Liu, Upland, CA (US)

(73) Assignee: City of Hope, Duarte, CA (US)

( * ) Notice: Subject to any disclaimer, the term of this patent is extended or adjusted under 35 U.S.C. 154(b) by 750 days.

(21) Appl. No.: 13/049,691

(22) Filed: Mar. 16, 2011

(65) Prior Publication Data

US 2011/0262920 A1 Oct. 27, 2011

Related U.S. Application Data

(60) Provisional application No. 61/314,511, filed on Mar. 16, 2010.

(51) Int. Cl.
C12Q 1/68 (2006.01)

(52) U.S. Cl.
CPC ........ *C12Q 1/6886* (2013.01); *C12Q 2600/118* (2013.01); *C12Q 2600/156* (2013.01)

(58) Field of Classification Search
None
See application file for complete search history.

(56) References Cited

PUBLICATIONS

Taya et al. (1984) The EMBO journal vol. 3 No. 12 pp. 2943.*
Slebos et al. (1990) The New England Journal of Medicine vol. 323 No. 9 pp. 561-565.*
Liu et al. (2004) Biotechniques vo. 37: pp. 360-364.*
Tonon et al. (2005) PNAS vol. 102 No. 27 pp. 9625-9630 and online www.pnas.org/cgi/doi/10.1073/pnas.0504126102.*
Jancik et al. (published on line on Jun. 7, 2010) J of Biomedicine and Biotechnology vol. 2010 article ID 150960 13 pages doi:10.1155/2010/150960.*
Chiang, D. Y., et al., "High-Resolution Mapping of Copy-Number Alterations with Massively Parallel Sequencing," Nat. Methods 6(1):99-103 (2009).
Croce, C. M., "Oncogenes and Cancer," New Eng. J. Med. 358:502-511 (2008).
Duelli, D., et al., "Cell Fusion: A Hidden Enemy?" Cancer Cell 3:445-448 (2003).
Fauth, C., et al., "Classifying by Colors: FISH-Based Genome Analysis," Cytogenet. Cell Genet. 93:1-10 (2001).
Herbst, R. S., et al., "Lung Cancer," N. Engl. J. Med. 359:1367-1380 (2008).
Jemal, A., et al., "Cancer Statistics, 2008," CA Cancer J Clin 58:71-96 (2008).
Kallioniemi, O.P., et al., "Optimizing Comparative Genomic Hybridization for Analysis of DNA Sequence Copy Number Changes in Solid Tumors," Genes Chromosomes & Cancer 10:231-243 (1994).
Langmead, B., et al., "Ultrafast and Memory-Efficient Alignment of Short DNA Sequences to the Human Genome," Genome Biology 10:R25 (2009).
Massarelli, E., et al., "KRAS Mutation Is an Important Predictor of Resistance to Therapy with Epidermal Growth Factor Receptor Tyrosine Kinase Inhibitors in Non-Small-Cell Lung Cancer," Clin. Cancer Res. 13:2890-2896 (2007).
Mertens, F., et al., "Chromosomal Imbalance Maps of Malignant Solid Tumors: A Cytogenetic Survey of 3185 Neoplasms," Cancer Res. 57:2765-2780 (1997).

(Continued)

*Primary Examiner* — Suchira Pande
(74) *Attorney, Agent, or Firm* — Perkins Coie LLP; Courtney Prochnow

(57) ABSTRACT

A method for survival prediction in cancer patients is provided. In one embodiment, the survival prediction is determined by the presence or absence of KRAS gene region deletion and/or loss of Chromosome 12 (Ch. 12) in cancer tumor tissue. In another embodiment, the presence or absence of KRAS gene region deletion and/or loss of Ch. 12 in cancer tumor tissue is used to predict survival in non-small-cell lung cancer (NSCLC) patients.

9 Claims, 4 Drawing Sheets

(56) References Cited

PUBLICATIONS

Nguyen, V. Q., et al., "A Large-Scale Validation of Dosage Analysis by Robust Dosage-Polymerase Chain Reaction," Analytical Biochem. 371:37-42 (2007).

Pinkel, D., et al., "High Resolution Analysis of DNA Copy Number Variation Using Comparative Genomic Hybridization to Microarrays," Nat. Genet. 20:207-211 (1998).

Sakuma, Y., et al., "Epidermal Growth Factor Receptor Gene Mutations in Atypical Adenomatous Hyperplasias of the Lung," Modern Pathology 20:967-973 (2007).

Salgia, R., et al., "Molecular Abnormalities in Lung Cancer," J. Clin. Oncol. 16:1207-1217 (1998).

Schrock, E., et al., "Multicolor Spectral Karyotyping of Human Chromosomes," Science 273:494-497 (1996).

Speicher, M. R., et al., "The Coloring of Cytogenetics," Nat. Med. 2(9):1046-1048 (1996).

Venkatraman, E. S., et al., "A Faster Circular Binary Segmentation Algorithm for the Analysis of Array CGH Data," Bioinformatics 23(6):657-663 (2007).

Zhu, C.Q., et al., "Role of Kras and EGFR as Biomarkers of Response to Erlotinib in National Cancer Institute of Canada Clinical Trials Group Study BR.21," J. Clin. Oncol. 26(26):4268-4275 (2008).

\* cited by examiner

METHODS FOR PREDICTING SURVIVAL IN CANCER PATIENTS

PRIORITY CLAIM

This application claims priority to U.S. Provisional Application No. 61/314,511, filed Mar. 16, 2010, the subject matter of which is hereby incorporated by reference as if fully set forth herein.

STATEMENT REGARDING FEDERALLY SPONSORED RESEARCH

The invention was made with Government support under Grant No. CA138359 Awarded by the National Cancer Institute (NCI), division of the National Institutes of Health (NIH). The Government has certain rights in the invention.

BACKGROUND

Non-small-cell lung cancer (NSCLC), accounting for about 85% of all lung cancers, is the leading cause of cancer deaths in the United States (Jemal et al., 2008) and worldwide. Despite advances in early detection and surgical resection, NSCLC often has a high recurrence.

KRAS is an oncogene located on Chromosome 12 (Ch. 12), with a cytogenic location of Ch. 12p12.1. KRAS encodes a protein called K-Ras that is involved in regulating cell division. The K-Ras protein has guanosinenucleotide-binding activity and intrinsic guanosine triphosphatase (GTPase) activity. K-Ras is downstream of epidermal growth factor receptor (EGFR), which signals through the PI3K/AKT/mTOR and STAT pathways involved in cell survival, and the RAS/RAF/MEK/MAPK pathway involved in cell proliferation.

The genetic code is a set of rules by which a gene is translated into a functional protein. Each gene includes a specific sequence of nucleotides encoded in a DNA (or sometimes RNA) strand. The four nucleotides are named for the heterocyclic base associated with them: adenine ("A"), cytosine ("C"), guanine ("G"), and thymine ("T"). The nucleotides polymerize to form a single strand of DNA, then two single strands interact by hydrogen bonding between complementary nucleotide, A being complementary with T and C being complementary with G, to form base pairs with results in the formation of a DNA double helix. RNA is similar to DNA except that the base thymine is replaced with uracil ("U") and does not form double strands.

A gene can contain coding and/or non-coding DNA sequences that are transcribed into RNA. RNA sequences that are transcribed by coding sequences of a gene are known as messenger RNA (mRNA). mRNA sequences in turn encode for a particular proteins by the process of translation. Proteins produced from genes then perform a specific biochemical or structural function. A correspondence between nucleotides, the basic building blocks of genetic material, and amino acids, the basic building blocks of proteins, must be established for genes to be successfully translated into functional proteins. Sets of three nucleotides, known as codons, each correspond to a specific amino acid or to a signal; three codons are known as "stop codons" wherein, instead of specifying a new amino acid, alert the translation machinery that the end of the gene has been reached. There are 64 possible codons (four possible nucleotides at each or three positions) and only 20 standard amino acids. Thus, the code is redundant and multiple codons can specify the same amino acid.

RNA sequences that are transcribed by non-coding sequences of a gene are known as non-coding RNA (ncRNA), and are not translated into proteins. There are several types of ncRNA that are involved in various cellular functions. For example, transfer RNA (tRNA) and ribosomal RNA (rRNA) are involved in protein assembly, small nuclear RNA (snRNA) and ribozymes are involved in post-transcriptional processing and splicing of mRNA, and MicroRNAs (miRNA), Piwi-interacting RNA (piRNA) and small interfering RNA (siRNA) are involved in gene regulation by acting via the RNA interference (RNAi) system. The RNAi system involves miRNA, siRNA, piRNA or other RNA molecules that are complementary to a target DNA and/or RNA sequence, and regulates gene expression in several ways. For example, an miRNA, siRNA or piRNA may bind to and effect or accelerate the degradation of a target mRNA, or may bind to a target DNA or RNA sequence to block or enhance transcription or translation, respectively.

A variance, also known as a polymorphism or mutation, in the genetic code for any coding or non-coding gene sequence may result in the production of a gene product, usually a protein or an RNA molecule, with altered biochemical activity or with no activity at all, or may influence the function of that gene or locus. This can result from as little change as an addition, deletion, or substitution of a single nucleotide in the DNA comprising a particular gene that is sometimes referred to as a single nucleotide polymorphism (SNP).

Somatic mutations in the KRAS gene are involved in the development of many types of cancer, including NSCLC. When mutated in codon 12, 13 or 61, the KRAS genes encode a constitutively active K-Ras protein that continuously activate transducer signals by linking tyrosine kinases to downstream serine and threonine kinases. Activating point mutations have been found in various malignancies, including NSCLC. In advanced NSCLC, tumors that harbor KRAS point mutations have been correlated with progression of the disease, but not with survival (Massarelli et al., 2007). While the EGFR tyrosine kinase inhibitors, gefitinib and erlotinib can be beneficial for some NSCLC patients, the presence of KRAS mutations predicts primary resistance to these drugs (Massarelli et al., 2007; Zhu et al., 2008; Herbst et al., 2008).

In addition, variations in gene dosage, the number of copies of a gene that are present in a cell, can be clinically significant indicators of disease states. Such variations arise from errors in DNA replication and can occur in germ line cells (leading to congenital defects and even embryonic demise), or in somatic cells. These replication anomalies can cause deletion or duplication of parts of genes, full-length genes and their surrounding regulatory regions, megabase-long portions of chromosomes, or entire chromosomes.

Chromosomal abnormalities affect gene dosage on a larger scale and can affect either the number or structure of chromosomes. Conditions wherein cells, tissues, or individuals have one or more whole chromosomes or segments of chromosomes either absent, or in addition to the normal euploid complement of chromosomes can be referred to as aneuploidy.

Chromosomal aberrations in somatic cells, such as large deletions, insertions or amplifications that are the result of acquired mutations such as loss of heterozygosity (LOH) or gene duplication are associated with many diseases, including many types of cancer. Because somatic KRAS gene mutations have been associated with the development of many types of cancer, including NSCLC, chromosomal aberrations of the KRAS gene are also likely to be clinically relevant in cancer research. Detection of such chromosomal aberrations may have therapeutic, diagnostic or prognostic implications in cancer patients.

Methods for the detection of point mutations and small deletions or insertions in genomic DNA have been well established, however, detection of larger genomic deletions or other aberrations is more complicated. Chromosomal aberrations can be detected in cancer through chromosomal banding (Mertens et al., 1997; Database of Aberrations in cancer, found at http://cgap.nci.nih.gov/Chromosomes/Mitelman), fluorescent in situ hybridization (FISH) (Schrock et al., 1996; Fauth and Speicher, 2001; Speicher and Ward, 1996), and comparative genomic hybridization (CGH) (Kallioniemi et al., 1994; Pinkel et al., 1998). However, early detection of deletions and amplifications are difficult, largely because 1) there is a low frequency of aberrations in early stages of cancer development, 2) tumors often have a multiploid cancer genome, and 3) early stage cancer tissue specimens often have low proportions of tumor cells. Therefore, there is a need to develop more accurate and reliable methods to detect chromosomal deletions and aberrations in early stages of cancer, which may be used in the detection and discovery of predictive biomarkers in cancer.

SUMMARY

A method for survival prediction in cancer patients is provided. In one embodiment, the survival prediction is determined by the presence or absence of a KRAS gene region deletion and/or loss of Chromosome 12 (Ch. 12) in cancer tumor tissue. In another embodiment, the presence or absence of a KRAS gene region deletion and/or loss of Ch. 12 in cancer tumor tissue is used to predict survival in non-small-cell lung cancer (NSCLC) patients.

In some embodiments, samples of cancer tumor tissue and optionally normal marginal tissue are harvested from cancer patients, and a first deletion detection technique is performed to detect gene region deletions in cancer tumor tissue. In one embodiment, the cancer patients are non-small-cell lung cancer (NSCLC) patients. In some embodiments, the first deletion detection technique that is used may be robust dosage-polymerase chain reaction (RD-PCR), fluorescent in situ hybridization (FISH), or comparative genomic hybridization (CGH). The results of the deletion detection technique are analyzed to determine whether a KRAS gene region deletion and/or loss of Chromosome 12 (Ch. 12) is present, wherein the presence of a gene region deletion or loss of Ch. 12 in the cancer tumor tissue that is not present in the normal marginal tissue is associated with a shorter survival.

In one embodiment, the deletion detection technique is RD-PCR, wherein a target gene region and control gene region are simultaneously amplified. The total number and relative ratio of gene or gene region template copies are determined by the ROY and ROT, then the ratio of ROT in tumor tissue to normal marginal tissue is calculated to determine whether a KRAS gene region deletion and/or loss of Ch. 12 is present. The presence of a gene region deletion or loss of Ch. 12 in the tumor tissue that is not present in the normal marginal tissue is associated with shorter survival. In another embodiment, a kit comprising all of the materials necessary to perform the method for predicting survival in NSCLC patients is contemplated.

DETAILED DESCRIPTION

Figure 1:
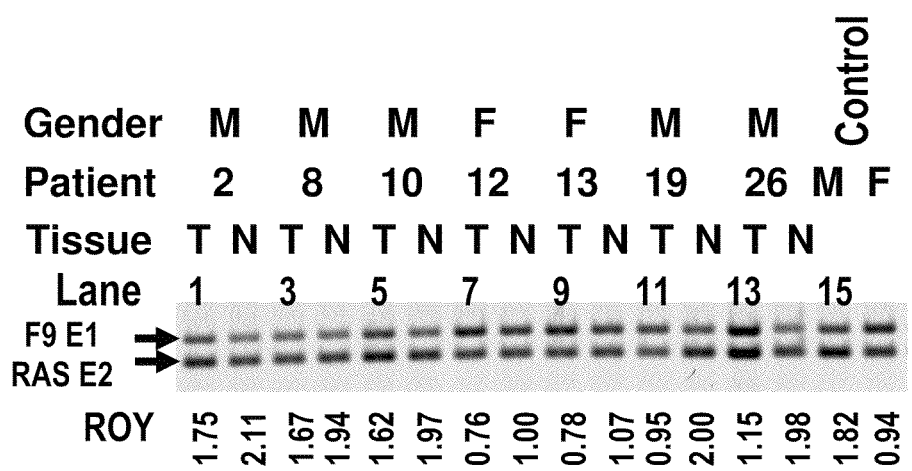
FIG. 1 illustrates the detection of deletions in the KRAS gene region. Exon 2 of the KRAS gene (target), and exon 1 of the F9 gene (endogenous internal control) were co-amplified from genomic DNA isolated from frozen cancer samples of NSCLC patients.

Methods for predicting survival in cancer patients are provided. In some embodiments, a survival prediction is determined by the presence or absence of KRAS gene region deletions and/or loss of Chromosome 12 (Ch. 12) in cancer tumor tissue compared to normal marginal tissue. In one embodiment, the methods for predicting survival are used to predict survival in early stage non-small-cell lung cancer (NSCLC) patients.

The term "gene region" as used herein refers to a gene, its exons, its introns, and its associated regions flanking it upstream and downstream, e.g., stop and start codons, and regulatory sequences such as promoters and enhances.

The term "gene" refers to a DNA sequence that comprises control and coding sequences necessary for the production of an RNA having a non-coding function (e.g., an rRNA, tRNA, miRNA, siRNA, piRNA, snRNA or ribozyme), or an RNA having a coding function (e.g., an mRNA) for a polypeptide. The RNA or polypeptide can be encoded by a full length coding sequence or by any portion or the coding sequence so long as the desired activity or function is retained.

The term "gene dosage" as used herein refers to the copy number of a gene, a gene region, a chromosome or fragments or portions thereof. Normal individuals carry two copies of most genes or gene regions, one on each of two chromosomes. However, there are certain exceptions, e.g., when genes or gene regions reside on the X or Y chromosomes, or when gene sequences are present in pseudogenes.

The term "aneuploidy" as used herein refers to conditions wherein cells, tissues, or individuals have one or more whole chromosomes or segments of chromosomes either absent, or in addition to the normal euploid complement of chromosomes.

Typically, human solid tumor cells have an aneuploidy, that is, they have an abnormal number of chromosomes or chromosome segments present within an individual cell. Tumor cells have been detected with an aneuploidy of 6n, including those in the studies described herein. When a single gene or gene region is knocked out, the dosage effect may cause a change in the aneuploidy. For example, if a single KRAS gene or gene region is knocked out in a 6n cell, the gene dosage effect is approximately a 15% reduction, and may influence aneuploidy, i.e., changes from 6n to 5n. In the studies described herein, a change in gene dosage of approximately 15% in cells, including aneuploid cells, unexpectedly resulted in an altered survival in oncology patients.

Methods for survival prediction in cancer patients as described herein comprise the use of one or more deletion detection techniques that can detect gene region or chromosomal deletions, the results of which can be used for determining a survival prediction. For example, a KRAS gene region deletion and/or loss of Chromosome 12 (Ch. 12) in tumor tissue that is not found in normal marginal tissue is associated with a shorter survival in NSCLC patients. In another embodiment, kits for use in predicting survival in early stage NSCLC are provided.

According to some embodiments, a cancer tumor tissue and optionally a normal marginal tissue are harvested from cancer patients undergoing resection surgery. A tissue is then analyzed by performing one or more deletion detection technique for the detection of KRAS gene region deletions and/or loss of Ch. 12. Several deletion detection techniques exist to detect such deletions and losses. The deletion detection technique may be any suitable method for detecting nucleic acids. In some embodiments, the deletion technique may detect alteration in RNA form or expression or alterations in a region of DNA.

In some embodiments, methods for nucleic acid detection described herein include amplification or signal amplification methods. Amplification of target DNA or RNA sequences in a tissue sample may be accomplished by any suitable method known in the art, such as transcription amplification, reverse transcription polymerase chain reaction (RT-PCR) amplification, quantitative PCR or RT-PCR, ligase chain reaction, self-sustained sequence replication, transcriptional amplification system, Q-Beta Replicase, rolling circle replication or any other nucleic acid amplification method, followed by the detection of the amplified molecules using known techniques as described below. Such methods are useful for the detection of nucleic acid molecules if such molecules are present in very low numbers. In some aspects, expression is assessed by quantitative fluorogenic RT-PCR (i.e., the TaqMan® System).

In some embodiments, expression levels of RNA or DNA may be detected using a membrane blot (such as used in hybridization analyses such as Northern, Southern, dot, and the like), or microwells, sample tubes, gels (e.g. electrophoresis), beads or fibers (or any solid support comprising bound nucleic acids). The detection of nucleic acid expression may also include using nucleic acid probes in solution.

In some embodiments, detection of nucleic acids may be accomplished by a sequence-specific probe hybridization technique used in conjunction with or without an amplification step. The term "probe" refers to any molecule that is capable of selectively binding to a specifically intended target biomolecule, for example, a nucleotide transcript or a protein encoded by or corresponding to a biomarker. Examples of molecules that can be utilized as probes include, but are not limited to, RNA, DNA, proteins, antibodies, and organic molecules. Probes and primers for the hybridization techniques described above can be synthesized and labeled by various known techniques. For example, oligonucleotides for use as probes and primers may be chemically synthesized according to the solid phase phosphoramidite triester method or using an automated synthesizing technique. Purification of oligonucleotides can be performed, e.g., by either native acrylamide gel electrophoresis or by anion-exchange HPLC.

In some aspects, the hybridization methods may include, but are not limited to, solution phase, solid phase, oligonucleotide array methods, mixed phase, or in situ hybridization assays. In solution (or liquid) phase hybridizations, both the target nucleic acid and the probe or primers are free to interact in the reaction mixture. Techniques such as real-time PCR systems have also been developed that permit analysis, e.g., quantification of amplified products during a PCR reaction. In this type of reaction, hybridization with a specific oligonucleotide probe occurs during the amplification program to identify the presence of a target nucleic acid. Examples of real-time PCR systems include fluorescence resonance energy transfer hybridization probes, molecular beacons, molecular scorpions, and exonuclease hybridization probes.

Hybridization complexes may be detected according to various techniques. For example, nucleic acid probes capable of specifically hybridizing to a target can be labeled by any one of several methods typically used to detect the presence of hybridized nucleic acids. For example, one common method of detection is the use of autoradiography using probes labeled with 3H, 125I, 15S, 14C, or 32P, or other suitable labels. Alternatively, probes can be conjugated directly with labels such as fluorophores, chemiluminescent agents or enzymes. The choice of label depends on sensitivity required, ease of conjugation with the probe, stability requirements, and available instrumentation.

In one embodiment, the RNA is immobilized on a solid surface and contacted with a probe, for example by running the isolated RNA on an agarose or other gel and transferring the RNA from the gel to a membrane, such as nitrocellulose. In an alternative embodiment, the probe(s) are immobilized on a solid surface and the RNA is contacted with the probe(s), for example, in an Affymetrix gene chip array.

In other embodiments, microarrays are used to detect biomarker expression. DNA microarrays provide one method for the simultaneous measurement of the expression levels of large numbers of genes. Each array consists of a reproducible pattern of capture probes attached to a solid support. Labeled RNA or DNA is hybridized to complementary probes on the array and then detected by laser scanning. Hybridization intensities for each probe on the array are determined and converted to a quantitative value representing relative gene expression levels. High-density oligonucleotide arrays are useful for determining the gene expression profile for a large number of RNAs in a sample.

In some embodiments, the deletion detection technique, includes robust dosage-polymerase chain reaction (RD-PCR), fluorescent in situ hybridization (FISH), and comparative genomic hybridization (CGH).

RD-PCR. In one embodiment, the number of copies of a target or control gene region or a chromosome within a tumor cell may be determined by robust dosage-polymerase chain reaction (RD-PCR). RD-PCR is a duplex quantitative PCR that co-amplifies a target gene, gene region, or locus ("target") and an endogenous internal control gene, gene region, or locus ("control") from the same genomic DNA source (Liu et al., 2003; Nguyen et al., 2007). The control has a known gene copy number per cell since it its gender is known, while the target has an unknown dosage number per cell. For example, if the target is autosomal, then the control is X-chromosomal. In one embodiment, the target gene region may be exon 2 or exon 3 of the KRAS gene. In another embodiment, the control gene region is exon 1 of the F9 gene.

In accordance with embodiments of the disclosure, RD-PCR products are analyzed to determine the relative template copy number quantitatively. The target and control genes or gene regions are compared in order to determine whether a KRAS gene region deletion and/or loss of Ch. 12 is present. The ratio of yield (ROY) is directly proportional to the ratio of the target to control product. Thus, the net signal of the target gene region is divided by the net control gene signal to obtain the ratio of yields (ROY). The accuracy of ROY is the degree of conformity of a ROY to its true ROY value. The consistency of ROY is the degree to which further ROY will show the same or similar results, and is characterized in terms of the standard deviation of ROY.

A DNA sample from a NSCLC patient tissue is then tested and its ROY is compared to the expected ratio from a matched gender control tissue to determine the relative template ratio of target to control. For females, the ratio of the template copy number of the autosomal (KRAS) to X chromosomal (F9) locus is 2:2. For males, the ratio of the template copy number of the autosomal (KRAS) to X chromosomal (F9) locus is 2:1, which is functionally equivalent to a heterozygous chromosomal deletion. A blinded analysis with normal male and female samples can be used to validate a given assay when multiple heterozygous deletions are unavailable. Therefore, by using wild-type male and female samples as controls, relative template (or copy) numbers of 2:1 and 2:2 are established, respectively. This relative template ratio of target to control is known as the template copy ratio (ROT). In addition to the ROY and ROT calculations, the percentage of tumor cells within a tissue can be calculated and used as an additional factor in an analyzing whether a KRAS gene region deletion and/or loss of Ch. 12 is present.

Although other polymerase chain reaction (PCR) based methods can be used to detect chromosomal deletions and duplications, these methods have remained a challenge because of small variations in PCR efficiency accumulate exponentially with cycling, and the presence of a terminal plateau phase where PCR yield is saturated. These challenges are potentiated by preferential amplification of one segment over another, especially with high GC contents. In contrast, RD-PCR has advantages over other methods of PCR, such as: 1) high accuracy and consistency, 2) easy calibration of linearity using male and female samples, 3) use of an endogenous internal dosage control to eliminate preparation and manipulation errors, and 4) quantification of gene dosage over a wide dynamic range.

Fluorescent in situ hybridization (FISH). In another embodiment, the number of copies of a target or control gene or gene region or a chromosome within a tumor cell may be determined by FISH. FISH is a cytogenetic technique used to detect and localize the presence or absence of specific DNA sequences on chromosomes. FISH uses fluorescent probes that bind particular genes, gene regions or chromosome loci. The probe or probes are labeled by various methods, such as nick translation, random primed labeling, and PCR. Two labeling strategies are commonly used: indirect labeling, wherein probes are labeled with modified nucleotides that contain a hapten; and direct labeling, wherein nucleotides that have been directly modified to contain a fluorophore are used. The target gene, gene region, or locus and the probe are then denatured with heat or chemicals in order to allow annealing to occur between the complementary target and probe sequences. The probe and target sequences are then combined so that the probe hybridizes to its complementary sequence on the chromosome. In some embodiments, a fluorescent probe can be used to detect the site of hybridization directly. In other embodiments, the probe is not fluorescent, and a secondary fluorescent probe is used to visualize the hybridized probe. Hybrids formed between the probes and their chromosomal targets are then detected using a fluorescent microscope.

Comparative genomic hybridization (CGH). In another embodiment, the number of copies of a target gene or gene region; control gene or gene region; or chromosome within a tumor cell may be determined by CGH. CGH is a molecular-cytogenic method for the analysis of copy number changes in a subject's DNA. DNA from a subject's target tumor tissue and from normal marginal tissue is labeled with different colors. After combining the target tumor tissue and the normal marginal tissue DNA with unlabeled human cot-1 DNA (placental DNA that is enriched for repetitive DNA sequences) to suppress repetitive DNA sequences, the combination is hybridized to normal metaphase chromosomes. For array- or matrix-CGH, the combination is hybridized to a slide containing hundreds or thousands of defined DNA probes. Using epifluorescence microscopy and quantitative image analysis, regional differences in the fluorescence ratio of gains or losses as compared to the control DNA can be detected and used for identifying abnormal regions in the genome.

Gene region deletions and/or loss of Ch. 12 may be verified by performing a first technique described above, then performing a second technique described above to verify the results of the first technique. For example, RD-PCR may be performed first, the results of which may be verified by performing FISH. Alternatively, the gene region deletions detected by one or more of the techniques described above may be verified by a gene sequencing technique such as Illumina parallel sequencing analysis as described in the examples below. Other suitable gene sequencing techniques known in the art may include, but are not limited to, the Sanger method (e.g., chain terminator or dye terminator methods), high-throughput parallelized sequencing, and sequencing by hybridization, ligation, mass spectrometry, or electron microscopy.

The detection of KRAS gene region deletions or loss of Ch. 12 may be used to predict survival in NSCLC patients. Deletions found in cancer tumor tissue, but not in the corresponding normal tissue are associated with a decrease in survival. In one embodiment, a search for predictive survival biomarkers in early stage non-small-cell lung cancer (NSCLC) patients was performed by using the highly quantitative RD-PCR technique described above to detect KRAS gene region deletions or loss of Ch. 12 in cancer tumor tissue as compared to normal marginal tissue. In one embodiment, a KRAS gene region deletion or loss of Ch. 12 was determined to exist in cancer tumor tissue as compared to normal marginal tissue, by dividing the cancer tumor tissue ROT by the normal marginal tissue ROT (T/N ROT). If the T/N ROT falls below a threshold (set at 0.85, see examples below), then it is likely that a KRAS gene region deletion or loss of Chromosome 12 exists in the cancer tumor tissue, but not in the normal marginal tissue. In one example, seven such deletions were found in 28 surgical sectioned cancer tissues but not in their paired normal tissues. These seven patients had a median survival or 35 months after surgery, compared with non-deletion patients of 59 months, showing a 1.7-fold decrease in survival (Long-Rank test; P=0.045).

Having described the invention with reference to the embodiments and illustrative examples, those in the art may appreciate modifications to the invention as described and illustrated that do not depart from the spirit and scope of the invention as disclosed in the specification. The Examples are set forth to aid in understanding the invention but are not intended to, and should not be construed to limit its scope in any way. The examples do not include detailed descriptions of conventional methods. Such methods are well known to those of ordinary skill in the art and are described in numerous publications. Further, all references cited above and in the examples below are hereby incorporated by reference in their entirety, as if fully set forth herein.

EXAMPLE 1

Materials and Methods

NSCLC patients and tissue specimens. Twenty-eight NSCLC patients from Taiwan were diagnosed at an early stage (IA, IB, IIA, or IIB) and were treated with standard adjuvant therapy (Table 1). Tissues were harvested during resection surgery, wherein samples of the cancer tissue and the paired marginal normal tissue were removed form each patient, sectioned, and then immediately frozen at −70° C. The cancer tissues contained sufficient portion of tumor cells, typically ≥40%, and normal tissues had no tumor cells as initially judged by a pathologist.

Extraction of genomic DNA from frozen tissues. The genomic DNA was extracted from frozen tissue using DNeasy Mini Kit according to manufacturer's protocol (Qiagen). The concentrations were measured by NanoDrop-1000 spectrophotometer at 260 nm (NanoDrop).

RD-PCR for chromosomal deletions. Each assay co-amplified a KRAS segment as a target and an X-Chromosome segment as an endogenous internal control. Primers were designed according to Liu et al. 2003 and Nguyen et al., 2007 (Nguyen et al., 2007; Langmead et al. 2009), the details of which are shown in Table 2 below.

TABLE 1

Seven deletions and clinical characteristics of early stage NSCLC patients

| # | Sex | Age | Smoking (PPD) | Follow up (M) | Recurrence/ Metastasis | Status | Histology | Differentiation | Stage | Lymph node involved | Tumor size | KRAS gene region deletion |
|---|-----|-----|---------------|---------------|-----------------------|--------|-----------|-----------------|-------|--------------------|-----------|-------------------------|
| 1 | F | 62 | No | 53 | | Alive | Adenoca | Moderate | IB | N0 | T2 | |
| 2 | M | 65 | Yes | 47 | | Alive | Adenoca | Moderate | IA | N0 | T1 | Del |
| 3 | M | 74 | Yes | 22 | Brain | Death | Squamous | Poor | IB | N0 | T2 | |
| 4 | M | 56 | Yes | 51 | | Alive | Squamous | Moderate | IB | N0 | T2 | |
| 5 | M | 76 | Yes | 26 | | Loss follow up | Adenoca | Moderate | IB | N0 | T2 | |
| 6 | M | 58 | No | 48 | | Alive | Adenoca | Moderate | IA | N0 | T1 | |
| 7 | M | 70 | No | 6 | | Death | Squamous | Moderate | IA | N0 | T1 | |
| 8 | M | 70 | No | 27 | | Death | Adenoca | Moderate | IB | N0 | T2 | Del |
| 9 | M | 70 | No | 48 | | Alive | Squamous | Moderate | IA | N0 | T1 | |
| 10 | M | 65 | Yes | 56 | Lung | Death | Squamous | Moderate | IB | N0 | T2 | Del |
| 11 | M | 46 | No | 6 | | Loss follow up | Squamous | Poor | IB | N0 | T2 | |
| 12 | F | 72 | No | 38 | Mediastinum LN | Death | Adenoca | Moderate | IA | N0 | T1 | Del |
| 13 | F | 80 | No | 32 | | Death | Adenoca | Moderate | IB | N0 | T2 | Del |
| 14 | F | 71 | No | 42 | Bone | Alive | Adenoca | Moderate | IB | N0 | T2 | |
| 15 | M | 51 | Yes | 70 | | Alive | Squamous | Moderate | IB | N0 | T2 | |
| 16 | M | 73 | No | 40 | | Alive | Adenoca | Moderate | IB | N0 | T2 | |
| 17 | M | 76 | Yes | 28 | | Loss follow up | Squamous | Moderate | IB | N0 | T2 | |
| 18 | F | 36 | No | 40 | | Alive | Adenoca | Moderate | IIB | N1 | T2 | |
| 19 | M | 69 | No | 24 | Lung | Death | Adenoca | Moderate | IA | N0 | T1 | Del |
| 20 | M | 63 | No | 45 | | Alive | Adenoca | Moderate | IA | N0 | T1 | |
| 21 | F | 72 | No | 34 | | Alive | Adenoca | Moderate | IA | N0 | T1 | |
| 22 | M | 77 | Yes | 34 | | Alive | Squamous | Moderate | IB | N0 | T2 | |
| 23 | F | 77 | No | 20 | | Death | Adenoca | Moderate | IA | N0 | T2 | |
| 24 | M | 65 | Yes | 31 | | Alive | Adenoca | Well | IA | N0 | T1 | |
| 25 | F | 48 | Yes | 65 | Lung | Death | Adenoca | Well | IB | N0 | T2 | |
| 26 | M | 81 | No | 18 | | Loss follow up | Adenoca | | IA | N0 | T1 | Del |
| 27 | M | 71 | No | 53 | | Alive | Adenoca | Moderate | IA | N0 | T1 | |
| 28 | M | 62 | No | 39 | Brain | Death | Squamous | Poor | IB | N0 | T2 | |

TABLE 2

Primers for RD-PCR

| Gene and exon | Name | 3' gene specific region of the primer Sequence (5'-3') | Tm (° C.) | Core segment Size (bp) | Core segment Tm (° C.) | Core segment GC (%) |
|---|---|---|---|---|---|---|
| F9 exon 1 on Ch.X (Control) | F9(2724)D | ATGTAGCCACTATGCCTATC (SEQ ID NO: 2) | 64.4 | 486 | 83.0 | 40.7 |
| | F9(3210)U | CTGGCTGTTAGACTCTTCAA (SEQ ID NO: 3) | 61.7 | | | |
| KRAS exon 2 on autosome 12p12.1 | RAS(5445)D | CTGGTGGAGTATTTGATAGTGT (SEQ ID NO: 4) | 61.9 | 413 | 80.4 | 34.9 |
| | RAS(5857)U | GAACATCATGGACCCTGACA (SEQ ID NO: 5) | 67.9 | | | |

TABLE 2-continued

Primers for RD-PCR

| Gene and exon | Name | 3' gene specific region of the primer | | Core segment | | |
|---|---|---|---|---|---|---|
| | | Sequence (5'-3') | Tm (° C.) | Size (bp) | Tm (° C.) | GC (%) |
| KRAS exon 3 on autosome 12p12.1 | RAS(23351)D | AGTGGCCATTTGTCCGTCAT (SEQ ID NO: 6) | 71.1 | 418 | 81.3 | 36.8 |
| | RAS(23768)U | GCATGGCATTAGCAAAGACT (SEQ ID NO: 7) | 66.4 | | | |

The primers are named according to the following protocol: gene(starting nucleotide # of gene)direction of transcription. For example, for the primer named F9(2724)D, F9 is the human coagulation factor IX gene, (2724) means that the 5' end of the 3' gene-specific region of the primer begins at nucleotide 2724 (according to GenBank accession K02402), and D means that the direction of the transcription is downstream. The precise sizes and locations of the PCR fragment can be obtained from the informative names. The KRAS sequence is from Genbank accession NG_007524 (SEQ ID NO:1). The sequence of the 3' gene-specific region of each primer is shown. A 10-nucleotide universal tail for KRAS primers (5'ggccaagtga3'; SEQ ID NO:8) was attached to the 5' end of each primer.

Oligo 5 calculates the melting temperature of a primer by the nearest neighbor method at 50 mM KCl, 0.7 mM free Mg, and 200 nm DNA. The melting temperature of a PCR product The $T_m$ value of each PCR segment was estimated under the above salt conditions by the formula:

$$T_m^{product} = 31.5 + 16.6 \log\{[K^+]/(1+0.7[K^+])\} + 0.41(\%G + \%C) - 500/\text{length}.$$

Before RD-PCR, genomic DNA samples were incubated at 95° C. in 1×Expand High Fidelity buffer #3 without MgCl$_2$ (Roche) for 10 minutes in order to completely denature the genomic DNA and minimize RD-PCR bias (Langmead et al., 2009).

Each RD-PCR reaction contained a total volume of 25 μl containing the following: 1×Expand High Fidelity buffer #3 (Roche), 4.5 mM MgCl$_2$, 200 μM each dNTP, 0.1 μM each primer of the F9 gene (internal control), 0.3 μM each primer for exon 2 or 0.2 μM each primer for exon 3 (target), 1U of Platinum Taq DNA polymerase and 1U of Platinum Taq DNA polymerase High Fidelity (Invitrogen), and 60 ng of genomic DNA. The reaction was first incubated at 94° C. for 2 minutes to denature the sample followed by the cycling phase, wherein each cycle follows a protocol of denaturation at 94° C. for 15 seconds, annealing at 55° C. for 30 seconds, and elongation at 72° C. for 90 seconds, repeated for 23 cycles.

Following the RD-PCR reaction, 15 μl of each reaction sample was loaded onto and electrophoresed through a 3% agarose gel. The gel was then stained with 0.5 μg/mL ethidium bromide for 1 hour, then scanned with a Typhoon™ 9410 Variable Mode Imager (GE healthcare) with the following parameter settings: 532 nm laser wavelength, 610 BP 30 emission filter, 550 photolnultiplier voltage, normal sensitivity, +3 mm focal plane, and 50 μm resolution.

The image of the gel was then analyzed using Imager-Quant™ software to quantify product yield. The net signal of a product was obtained by subtracting local background signal from total signal. The product yield ratio (ROY) of the KRAS gene to the F9 gene of a sample is the net signal of the target segment divided by the net signal of the control segment.

For normal samples, ROY was correlated with the template copy ratio (ROT) of the KRAS gene to the F9 gene (normal male ROT=2 and female ROT=1) and regressed according to the following linear equation:

$$ROY = m \cdot ROT + b.$$

The linear equation was then used to convert ROY of an unknown sample to its ROT. A threshold ROT value of ≤85% for a cancer sample was set by comparison with its paired normal marginal sample, equivalent to when 30% of diploid cells lose one copy of the KRAS gene.

Fluorescence in situ hybridization (FISH) analysis. Hematoxylin and eosin (H&E) stained frozen tissue sections were analyzed. Cover slips were removed in xylene and slides were fixed in Carnoy's fixative (3:1; methanol:acetic acid) for 30 min. Slides were then placed in 2×SSC for 10 min. followed by 0.05% pepsin in 10 mM HCl at 37° C. for 10 min.

After dehydration through an ethanol series, a Vysis EGFR/CEP 7 probe (cat# 30-191053) (Abbott Molecular, Abbott Park, Ill.) was applied. The probe and section were co-denatured at 80° C. for 5 minutes. A post-wash overnight incubation at 37° C. was then performed according to the manufacturer's instructions.

KRAS copy number was determined using the bacterial artificial chromosome (BAC) clone RP11-295i5 (Rosewell Park Microarray Core Facility). KRAS was nick translated with digoxigenin and detected with rhodamine anti-dig. This probe was combined with a Vysis CEP12 (cat# 32-132012) (Abbott Molecular, Abbott Park, Ill.) probe for an internal control. Hybridization was performed as described above.

Images were acquired using Bioview D3 image analyzer (Bioview) to capture the cell morphology. For each probe set, sixty cells were examined for each case by two independent scorers. Their average copies per tumor cell were normalized by positive normal standards, and then rounded to the nearest integer.

Pathological analysis. Frozen tissues were formalin fixed and paraffin embedded, then 5 μm thick sections were cut and placed on slides. The sections were then stained with hematoxylin and eosin (H&E). Morphological analyses were performed to determine the ratio of tumor area to the total area (% tumor cells) on slides by two investigators.

Illumina parallel sequencing analysis. Genomic DNA library preparation and high throughput sequencing were performed using the Solexa sequencing technology (GenomeAnalyzer, Illumina) according to the manufacturer's instructions. Five micrograms (μg) of genomic DNA was sheared using the bioruptor (Diagenode). The fragmented DNA was end-repaired using T4 DNA polymerase and Klenow polymerase with T4 polynucleotide kinase to phosphorylate the 5' ends. A 3' overhang was created using a 3'-5' exonuclease-deficient Klenow fragment, and Illumina paired-end adaptor oligonucleotides were ligated to the sticky ends thus created. The ligation mixture was amplified for 18 cycles with Solexa primers followed by electrophoresis on an agarose gel and 400±25 bp fragments were selected and purified using a QIAGEN Gel Extraction Kit. The same libraries were used for both single read and paired-end sequencing. Clusters were generated on the Illumina Cluster station according to the manufacturer's protocol. Clusters of PCR colonies were then sequenced on the Genome Analyzer II platform. FASTQ sequence files were generated using the Illumina pipeline 1.3.2 for images processing and base calling.

Raw sequences from Illumina GAII sequencer were trimmed to the first 45 high quality bases and aligned to human genome build (using NCBI Build 36.1 of the human genome) using Bowtie aligner with default settings (Langmead et al. 2009). Briefly, reads are considered mapped to the genome when there are less than 2 mismatches in the first 28 bases, and the maximum quality score of mismatched bases is less than 70. Only one alignment belonging to the best stratum is reported when a read can be aligned to multiple locations. All of the following analyses were done in R statistical environment. Each chromosome was divided into non-overlapping 50 kb windows and the number of aligned tags within each window were counted and compared between cancer and normal samples. The log2 ratio for each window was calculated as the log2 transformed ratio between tumor counts and normal counts, offset by 1. The log2 ratio data were then mean centered and segmented using a circular binary segmentation (CBS) algorithm implemented in the Bioconductor package "DNAcopy" to detect copy number abnormalities (CNA) with default settings (Venkatraman & Olshen 2007). Only segments with more than 10 windows and an absolute log2 ratio>=0.1 were selected as candidate CNAs. Due to the polyploidy nature of these samples, the normalization approach will result in regions with high gains (e.g. EGFR) having a log2 ratio close to 0.

PCR and Sanger sequencing for point mutations. The following primers were designed to amplify and sequence exons 2 and 3 of the KRAS gene:

```
Exon 2 Forward:
                              (SEQ ID NO: 9)
5'-CTGGTGGAGTATTTGATAGTGT-3'

Exon 2 Reverse:
                             (SEQ ID NO: 10)
5'-ACTCCCAAGGAAAGTAAAGTT-3';

Exon 3 Forward
               (RAS(23351)D; SEQ ID NO: 6)
5'-AGTGGCCATTTGTCCGTCAT-3'

Exon 3 Reverse
               (RAS(23768)U; SEQ ID NO: 7)
5'-GCATGGCATTAGCAAAGACT-3'
```

Each PCR sample reaction mixture contained a total volume of 25 µl of the following: 50 mM KCl, 10 mM Tris/HCl (pH 8.3), 1.5 mM $MgCl_2$, 200 µM each dNTP, 0.1 µM each primer listed above, 1U of TaqGold DNA polymerase (Invitrogen), and 20 ng of genomic DNA. Before cycling, the samples were incubated at 94° C. for 10 minutes to activate the TaqGold DNA polymerase. Each cycle sample was then cycled, wherein each cycle followed a protocol of denaturation at 94° C. for 15 seconds, annealing at 55° C. for 30 second, and elongation at 72° C. for 1 minute, repeated for 35 cycles.

The PCR product was purified using Amocon50 to remove the unincorporated primers and dNTPs. Two nanograms (ng) of the PCR product were sequenced using ABI 3730 fluorescent DNA sequencer and BigDye terminator chemistry V1.1 (Applied Biosystems) with the above PCR primers. Sequencher software (Gene Codes) was used to identify a point somatic mutation when its mutant peak had ≥18% of the wild-type peak height, which is the equivalent to when 30% of diploid cells contain a copy of the mutation.

Statistical analysis. Data was analyzed using the JMP Statistical Discovery Software version 7.0 (SAS Institute, Cary, N.C.). Group comparisons for continuous data were performed using t-tests for independent means or one-way analyses of variance. A Kaplan-meier analysis was employed to estimate survival of patients. Cox proportional Hazard models were used to adjust for covariate effects on the risk ratio. Statistical significance was set at $P<0.05$.

EXAMPLE 2

Detection of Seven Large KRAS Gene Region Deletions or Loss of Chromosome 12 (Ch. 12) by RD-PCR The use of highly quantitative RD-PCR to measure the gene copies in genomic DNA in 28 early stage NSCLC patients (as described above) reliably detected very small changes in the number of copies of the KRAS gene (i.e. "gene dosage") at a high linearity and correlation between the copy number of the input template and the yield of the output product. Measurement of the gene dosage of any other portion of the KRAS gene or gene region may also be attained in this manner. Changes in gene dosage as small as 10% were obtained in a large-scale validation of 110 successive RD-PCR assays (Liu et al., 2003; Nguyen et al., 2007).

RD-PCR was used to examine the ratio of gene copies between exon 2 or 3 of the KRAS gene (the target), and exon 1 of the F9 gene (the endogenous internal control) from the genomic DNA pool with high accuracy and consistency. As shown in FIG. 1, exon 2 of the KRAS gene and exon 1 of the F9 gene were co-amplified from genomic DNA isolated from the frozen cancer samples of NSCLC patients. After being electrophoresed on an agarose gel, the relative product ratio of target to control (ROY) was calculated. Comparison of a ROY between a cancer sample and its paired normal tissue of a given patient is one factor used to determine whether a KRAS gene region deletion (D) was present. The linear function and correlation determinant were obtained from 12 male and 6 female normal samples (ROY=0.961·ROT−0.042, $R^2$=0.973) showing high linearity and correlation. A normal male (M) has two copies of the KRAS gene and one copy of the F9 gene per cell, a normal female (F) has two copies of the KRAS gene and two copies of the F9 gene per cell.

The product yield ratio (ROY) of the KRAS gene to the F9 gene was then converted to the corresponding template copy ratio (ROT) (see Table 3, Table 4, below). A threshold for the presence of deletions was set to a 15% deviation from cancer sample ROT values as compared to their paired normal samples. This threshold is 3 times higher than its coefficient variance (CV). Analyzed in this manner, RD-PCR can detect one copy of deletions in 6-ploid tumor cells, accounting for ≥70% of cellular population.

To compare RD-PCR results on different gels, ROY of a sample was converted to its ROT based on a linear regression equation as described above. ROY was regressed and correlated with its ROT among 54 normal male samples (ROT=2, because there are two copies of the KRAS gene and one copy of the F9 gene in a male cell) and 27 female (ROT=1) samples. In the linear regression equation of ROY=m·ROT+ b, the average coefficient m was 1.12 and 1.05 for exons 2 and 3, showing a high correlation.

In addition, ROT was further statistically analyzed (Table 3). Coefficient variance of ROT among the normal samples was from 0.054 to 0.061. In other words, if an unknown ROT is ≤85% of the normal value, we have more than 99% confidence to detect a KRAS deletion. CV of ROT from the 7 tumor tissues is 0.32, an even smaller number.

TABLE 3

ROT statistics of the two RD PCR assays from normal samples

| Sex | Statistics | Normal sample | |
|---|---|---|---|
| | | Exon 2 | Exon 3 |
| Female | Average ROT | 0.995 | 1.020 |
| | Standard Deviation of ROT | 0.055 | 0.055 |
| | Coefficient Variance | 0.055 | 0.054 |
| | Number of sample | 19 | 8 |
| Male | Average ROT | 2.041 | 2.016 |
| | Standard Deviation of ROT | 0.109 | 0.124 |
| | Coefficient Variance | 0.054 | 0.061 |
| | Number of sample | 37 | 17 |

To exclude possible bias of the F9 gene dosage, its copies were calibrated by four additional RD-PCR assays that targeted four loci on Chromosome 7 (Ch. 7) within the EGFR and MET genes. In addition, the percentage of tumor cells within the cancer tissues was also measured.

Seven large KRAS gene region deletions or loss of the locus on Chromosome 12 (Ch. 12) were found in the frozen cancer tissues (~25% of cases), but not in their paired normal tissues. Specifically, in tumor cells, one to three copies of the KRAS gene were deleted from 4 or 6-ploid genome, such as in regions of the EGFR gene and Chromosome 7 centromere, likely due to cell fusion (Duelli & Lazebnik 2003). Table 4 shows the relevant calculations in patients with KRAS gene region deletions that led to this conclusion. Analysis of any given sample was repeated up to 4 times on the average. The presence of KRAS gene region deletions was estimated from the results of RD-PCR, % tumor cells within tissue specimen, and copies of the F9 gene per tumor cell, assuming that each tumor cell has the identical genomic pattern as well as each normal cell does. The results of the RD-PCR include the following measurements: ROT of KRAS to F9, which is the copy number ratio of the KRAS gene to the F9 gene; and T/N ROT which is the ratio between the ROT of the tumor tissue to the ROT of its paired normal tissue. A threshold of T/N ROT was set to be 0.85. This means that a T/N ROT for exon 2 or exon 3 that is 0.85 or lower indicates that a KRAS gene region deletion is likely present. The percentage of tumor cells in each sample (% tumor cells) was measured by dividing the tumor area by the total tissue area on slides. The number of copies of EGFR and KRAS genes (EGFR and KRAS) as well as the number of Ch. 7 and Ch. 12 (Ch. 7 Centromere and Ch. 12 Centromere) per tumor cell were initially estimated by FISH (see Example 3 below).

TABLE 4

Seven KRAS gene region deletions

| | | | RD-PCR | | | | | | FISH[e] | | |
|---|---|---|---|---|---|---|---|---|---|---|---|
| | | | Exon 2 | | Exon 3 | | | | | | |
| | | | ROT of | | ROT of | | | | | | |
| Patient# | Sex | Tissue | KRAS to F9[a] | T/N ROT[b] | KRAS to F9 | T/N ROT[b] | % tumor cells[c] | KRAS deletion[d] | EGFR | Ch. 7 Centro-mere | KRAS | Ch. 12 Centro-mere |
| 2 | Male | Cancer | 1.73 | 0.81 | 1.66 | 0.84 | 60-70% | Yes | 8 | 6 | 2 | 3 |
| | | Normal | 2.14 | | 1.99 | | | | | | | |
| 8 | Male | Cancer | 1.70 | 0.85 | 1.61 | 0.87 | 60-70% | Yes | 4 | 4 | 2 | 2 |
| | | Normal | 1.98 | | 1.84 | | | | | | | |
| 10 | Male | Cancer | 1.61 | 0.81 | 1.75 | 0.81 | 80% | Yes | 4 | 4 | 2 | 3 |
| | | Normal | 1.99 | | 2.15 | | | | | | | |
| 12 | Female | Cancer | 0.82 | 0.79 | 0.88 | 0.79 | 60% | Yes | 6 | 3 | 3 | 3 |
| | | Normal | 1.03 | | 1.11 | | | | | | | |
| 13 | Female | Cancer | 0.80 | 0.74 | 0.79 | 0.69 | 80% | Yes | 6 | 6 | 2 | 3 |
| | | Normal | 1.07 | | 1.15 | | | | | | | |
| 19 | Male | Cancer | 0.96 | 0.48 | 0.77 | 0.43 | 50-60% | Yes | 6 | 6 | 3 | 3 |
| | | Normal | 2.01 | | 1.79 | | | | | | | |
| 26 | Male | Cancer | 1.18 | 0.58 | 1.32 | 0.64 | 60% | Yes | 5 | 4 | 2 | 3 |
| | | Normal | 2.02 | | 2.05 | | | | | | | |

Figure 2:
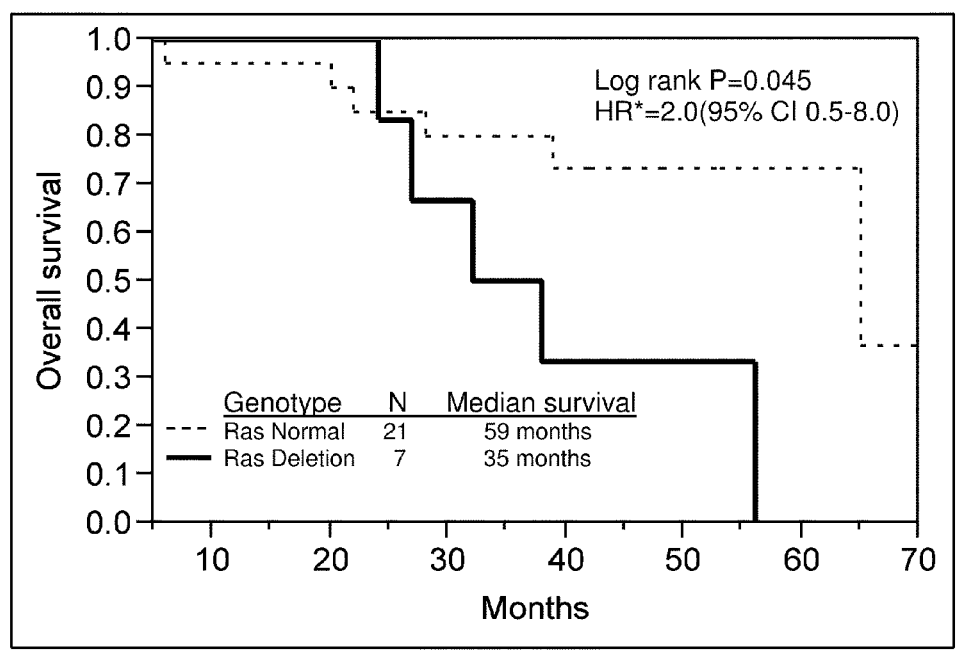
FIG. 2 is a graph illustrating the correlation between KRAS gene region deletions and survival rate in early stage NSCLC patients as analyzed by a Kaplan-Meier analysis and Cox hazard proportional model.

The NSCLC patients had over 5 years of clinical follow-up after surgery. The seven NSCLC patients with the KRAS gene region deletions had for a median survival of 35 months, while the remaining patients who did not have KRAS gene region deletions have a median survival of 59 months. (FIG. 2, Long-Rank test P=0.045). These results show a strong association between KRAS-gene region deletions and length of survival period, and suggest that the number of copies of the KRAS gene region (i.e. "gene dosage") is a predictive biomarker for survival in early stage NSCLC patients.

FIG. 2 is a graph illustrating that KRAS gene region deletions are correlated with a lower survival rate in early stage NSCLC patients. Kaplan-Meier analysis and Cox hazard pro portional models were applied to the above data for survival analysis. The solid line indicates the NSCLC patients with the KRAS gene region deletions (N=7), and dashed line indicates the NSCLC patients without KRAS gene region deletions (N=21).

EXAMPLE 3

KRAS Gene Region Deletions as Detected by FISH and Illumina Analyses

Figure 3:
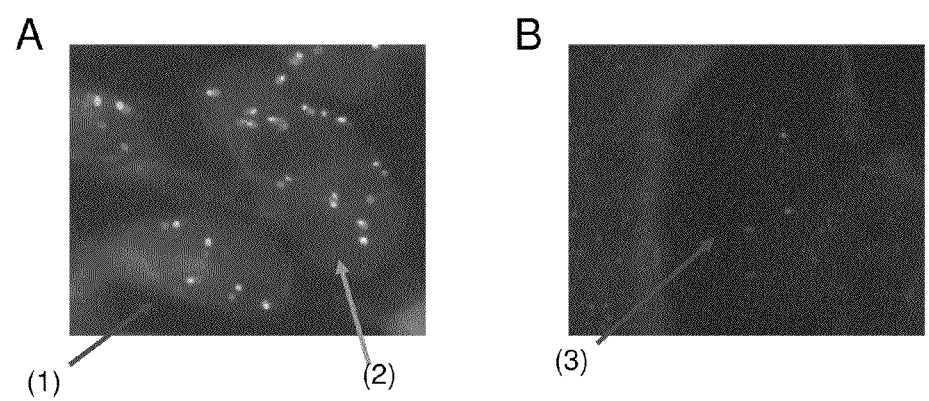
FIGS. 3A and 3B are representative FISH analyses according to embodiments of the disclosure.

The KRAS gene region deletions were verified by FISH by the use of an individual tumor cell as a unit to measure the copy ratio between the KRAS gene and Ch. 12 centromere. Deletions of any portions of the KRAS gene or gene region may be verified in this manner. FIGS. 3A and 3B are representative FISH analyses according to embodiments of the disclosure. FIG. 3A is an EGFR/CEP7 FISH image from patient 2 cancer tissue. The VYSIS EGFR probe was labeled in Spectrum orange (gray dots) and the CEP 7 centromere probe was labeled in Spectrum green (bright white spots). The cell on the lower left (arrow (1)) has a 5R/5G signal pattern. The cell in the middle right (arrow (2)) has a 6R/6G signal pattern.

FIG. 3B is a KRAS/CEP 12 FISH image from patient 13 cancer tissue. KRAS is labeled with Digoxigenin and detected with Rhodamine Anti Dig (red signal). The VYSIS CEP12 probe for the Ch. 12 centromere is labeled with Spectrum Green. The cell (arrow (3)) shows a 2R/3G pattern indicating a loss of 1 copy of the KRAS gene. (also see Table 4). This is based on the following reasons. First, tumor cells contained multi-copies of the genome, (commonly 4 or 6-ploid), such as in the EGFR gene and Ch. 7 centromere. Second, the KRAS gene showed two copies but Ch. 12 centromere had three copies in four cancer tissues, which directly implicates KRAS gene region deletions. In the other three cases, copies of the KRAS gene and Ch. 12 centromere were greatly reduced relative to those of the EGFR gene and Ch. 7 centromere, which indirectly implicates KRAS gene region deletions.

Although both RD-PCR and FISH show KRAS gene region deletions, there may be a difference in terms of the exact number of the KRAS genes deleted or lost (Table 4) presumably due to technical limitations. Because FISH examines tumor cells on slides with a thickness of 5 μm and not within the tumor as a whole, the number of signals may be underestimated. For example, if a large deletion spans the KRAS gene region and Ch. 12 centromere, the ratio may still remain normal.

Figure 4:
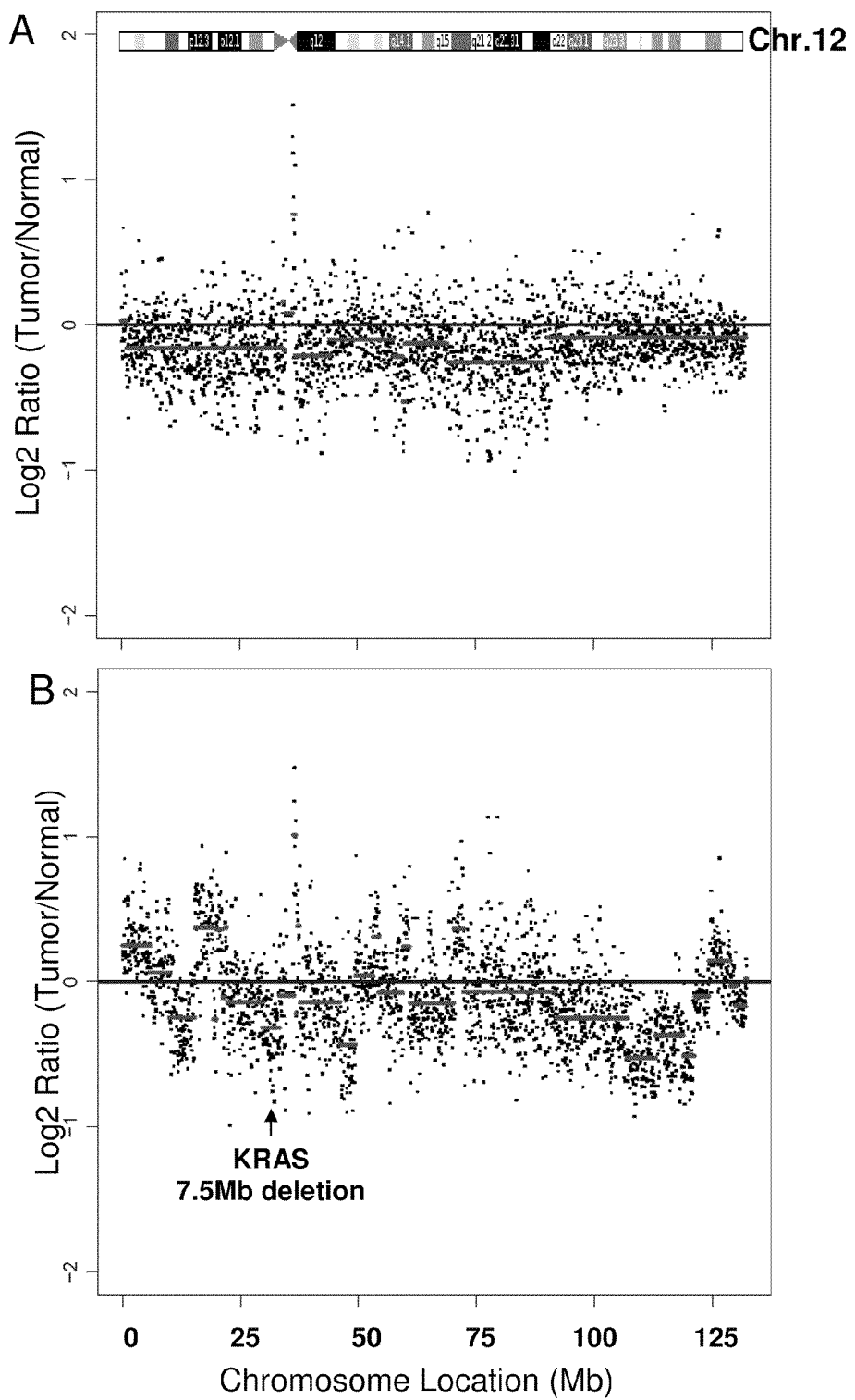
FIGS. 4A and 4B are representative Illumina analyses according to embodiments of the disclosure. Illumina parallel sequencing confirms the presence of KRAS gene region deletions in cancer samples of patients 13 (FIG. 4A) and 19 (FIG. 4B).

The KRAS gene region deletions were also verified by Illumina paired-end parallel sequencing as described above. About 20 million reads were scored from tumor and normal samples of patients 13 and 19 using a fixed window approach (Chiang et al., 2009) and CBS segmentation method. As shown in FIGS. 4A and 4B, Illumina parallel sequencing confirms the presence of KRAS gene region deletions in cancer samples of patients 13 and 19. Using a 50 kb non-overlapping window along the entire genome, the number of counts was scored for each window as a log2 function and then compared to that of the relative normal control. The log2 ratio data were then mean centered and segmented, represented by short red lines. Deletion within the KRAS locus is noted. The blue horizontal line at zero means that there is no change in the number of copies. Patient 13 had a large KRAS gene region deletion almost covering the entire short arm of Chromosome 12, while patient 19 has many more break points and hence a relatively small KRAS gene region deletion. The average log2 ratios at these deleted regions are −0.16 and −0.14 respectively, which is consistent with an estimation of a one copy loss in the 6-ploid genome.

EXAMPLE 4

Somatic KRAS Point Mutations Are Likely Not Predictive of Survival

Applying PCR and Sanger sequencing of exons 2 and 3 to patient 25 (Table 1), a G5571C somatic missense mutation (Gly to Ala at codon 12) was identified in the cancer tissue but not in the paired normal tissue. In addition, this patient did not harbor any KRAS gene region deletions.

In statistical analysis, if this patient is excluded from statistical analyses, the KRAS gene region deletion effect results in the same conclusion using only the data from the other patients. However, if the patient with a somatic KRAS point mutation is placed in the same category as a KRAS gene region deletion and transferred to the KRAS gene region deletion group, there would be no significant difference between the two groups (Long-Rank test, P=0.11). This suggests that KRAS point mutations are not necessarily predictive of survival, and that deletions and point mutations likely play different roles in the development of NSCLC.

KRAS point mutations are found much more frequently in advanced NSCLC or their cell lines. This difference may be caused by staged mutagenesis in cancer development. Furthermore, it has also been observed that the number of deletions typically is small in premalignant, hyperproliferative lesions but become substantially larger in more advanced lesions. For example, KRAS mutations can occur in atypical hyperplasias of the lung (Sakuma et al., 2007), but their number is 20-30% higher in advanced NSCLC (Salgia and Skarin, 1998).

References

The references listed below, and all references cited in the specification are hereby incorporated by reference in their entirety, as if fully set forth herein.

Chiang D Y, Getz G, Jaffe D B, O'Kelly M J, Zhao X, Carter S L, Russ C, Nusbaum C, Meyerson M, Lander E S (2009) High-resolution mapping of copy-number alterations with massively parallel sequencing. Nat Methods 6:99-103.

Croce C M (2008) Oncogenes and cancer. The New England journal of medicine 358:502-511.

Duelli D, Lazebnik Y: Cell fusion: a hidden enemy? Cancer Cell 3:445-8, 2003.

Fauth C, Speicher M R (2001) Classifying by colors: FISH-based genome analysis. Cytogenetics and Cell Genetics 93:1-10.

Herbst R S, Heymach J V, Lippman S M (2008) Lung cancer. The New England Journal of Medicine 359:1367-1380.

Jemal A, Siegel R, Ward E, Hao Y, Xu J, Murray T, Thun M J (2008) Cancer Statistics, 2008. CA: A Cancer Journal for Clinicians 58:71-96.

Kallioniemi O P, Kallioniemi A, Piper J, Isola J, Waldman F M, Gray J W, Pinkel D (1994) Optimizing comparative genomic hybridization for analysis of DNA sequence copy number changes in solid tumors. Genes, Chromosomes & Cancer 10:231-243.

Langmead B, Trapnell C, Pop M, Salzberg S L (2009) Ultrafast and memory-efficient alignment of short DNA sequences to the human genome. Genome Biol. 10:R25.

Liu Q, Li X, Chen J S, Sommer S S (2003) Robust dosage-PCR for detection of heterozygous chromosomal deletions. BioTechniques 34:558-568.

Massarelli E, Varella-Garcia M, Tang X, Xavier A C, Ozburn N C, Liu D D, Bekele B N, Herbst R S, Wistuba, I I (2007) KRAS mutation is an important predictor of resistance to therapy with epidermal growth factor receptor tyrosine kinase inhibitors in non-small-cell lung cancer. Clin Cancer Res 13:2890-2896.

Mertens F, Johansson B, Hoglund M, Mitelman F (1997) Chromosomal imbalance maps of malignant solid tumors: a cytogenetic survey of 3185 neoplasms. Cancer Research 57:2765-2780.

Nguyen V Q, Liu Q, Sommer S S (2007) A large-scale validation of dosage analysis by robust dosage-polymerase chain reaction. Analytical Biochemistry 371:37-42.

Pinkel D, Segraves R, Sudar D, Clark S, Poole I, Kowbel D, Collins C, Kuo W L, Chen C, Zhai Y, Dairkee S H, Ljung B M, Gray J W, Albertson D G (1998) High resolution analysis of DNA copy number variation using comparative genomic hybridization to microarrays. Nature Genetics 20:207-211.

Sakuma Y, Matsukuma S, Yoshihara M, Nakamura Y, Nakayama H, Kameda Y, Tsuchiya E, Miyagi Y (2007) Epidermal growth factor receptor gene mutations in atypical adenomatous hyperplasias of the lung. Mod Pathol. 20:967-973.

Salgia R, Skarin A T (1998) Molecular abnormalities in lung cancer. J Clin Oncol. 16:1207-1217.

Schrock E, du Manoir S, Veldman T, Schoell B, Wienberg J, Ferguson-Smith M A, Ning Y, Ledbetter D H, Bar-Am I, Soenksen D, Garini Y, Ried T (1996) Multicolor spectral karyotyping of human chromosomes. Science (New York, N.Y. 273:494-497.

Speicher M R, Ward D C (1996) The coloring of cytogenetics. Nature medicine 2:1046-1048.

Venkatraman, E. S. and Olshen, A. B. (2007). A faster circular binary segmentation algorithm for the analysis of array cgh data. Bioinformatics, 23:657-663.

Zhu C Q, da Cunha Santos G, Ding K, Sakurada A, Cutz J C, Liu N, Zhang T, Marrano P, Whitehead M, Squire J A, Kamel-Reid S, Seymour L, Shepherd F A, Tsao M S (2008) Role of KRAS and EGFR as biomarkers of response to erlotinib in National Cancer Institute of Canada Clinical Trials Group Study BR. 21. J Clin Oncol 26:4268-4275.

What is claimed is:

1. A method for predicting survival in a cancer patient comprising:
  (a) performing a first deletion detection technique on a cancer tumor tissue sample from a cancer patient, wherein the first deletion detection technique is robust dosage-polymerase chain reaction (RD-PCR) comprising:
    amplifying a target gene region comprising one or more exons of a Kirsten rat sarcoma viral oncogene homolog (KRAS) gene region to produce DNA molecules that are complementary to the sequence of the one or more exons using one or more set of primers selected from:
      a set of primers to amplify exon 2 of the KRAS gene region comprising the sequences of CTGGTGGAGTATTTGATAGTGT (SEQ ID NO:4) and GAACATCATGGACCCTGACA (SEQ ID NO:5), and
      a set of primers to amplify exon 3 of the KRAS gene region comprising the sequences of AGTGGCCATTTGTCCGTCAT (SEQ ID NO:6) and GCATGGCATTAGCAAAGACT(SEQ ID NO:7);
  (b) determining whether a KRAS gene region deletion is present; and
  (c) predicting about a 1.7-fold decrease in survival for a patient having a KRAS gene region deletion in the cancer tumor tissue.

2. The method of claim 1, wherein the cancer patient has non-small-cell lung cancer (NSCLC).

3. The method of claim 1, wherein the RD-PCR technique comprises co-amplifying the target gene region and a control gene region from the cancer tumor tissue sample.

4. The method of claim 3, wherein the control gene region is exon 1 of the F9 gene.

5. The method of claim 3, wherein the RD PCR results are quantified by determining the target gene region to control gene template copy ratio (ROT).

6. The method of claim 1, wherein the method further comprises a second deletion detection technique to verify the results of the first deletion detection technique.

7. The method of claim 6, wherein the second deletion detection technique is selected from the group consisting of robust dosage-polymerase chain reaction (RD-PCR), fluorescent in situ hybridization (FISH), and comparative genomic hybridization (CGH).

8. The method of claim 1, wherein the method further comprises performing a gene sequencing technique to verify the results of the first deletion detection technique.

9. The method of claim 2, wherein the patient has early stage NSCLC (IA, IB, IIA, or IIB).

* * * * *

```
                       SEQUENCE LISTING

<160> NUMBER OF SEQ ID NOS: 10

<210> SEQ ID NO 1
<211> LENGTH: 52675
<212> TYPE: DNA
<213> ORGANISM: Homo sapiens

<400> SEQUENCE: 1
caaacagaaa gacaaaaagg tgctgggtga gaaaaggagc agagacataa ataaaatatc      60
caattttaag ggtatagaga ggggattcac tcaaggaggg gagaccatct atctgctttg     120
agaagctggg aaacaaagtc ataggtcag gatggtgcct gactatggat gctctcaaaa     180
gctaggcacc aaggatttgg actggattca gctggatata agaagttatt acagacttgg     240
aagcaagatt aagtctccgg gaaggggaga cttaactggg accagagatc attttcccct     300
ataattttaa aggtacttat catctttagg tactcattag gtacttagct tgtaactctt     360
tccactgttc aaatatatac ccagtatgca tgtagcctat atggagcagg cacagagtaa     420
atgtttgatg atgataaaag acatgcggaa gaaaggttaa tttggcaaca tcataaaact     480
gaattgagac aaagaaagcc aggaggtagg aaagtcaatg aagaagttat tccagaaatg     540
tagctgagaa ggaaggaata cagaagaggc agatatggga aaatactcag gaagtataat     600
taaaaggagc tgtgactaat tttaataagg actgggttaa aaattaagtt ttcatgtcta     660
aatgttctgg aggaccatga tgtcactcag gtaagatgga ggaattgaga gagggaattc     720
gttagaggga ataacatggg gaatttggct ttggacaggc atttgccatg ataacagaat     780
attcatttag aaatggtcca ggaaattggt ttgatgagaa tgaagtgcct gtgaagagag     840
aggactgaag cttgttataa tttcattcac ttcaggaata tttacagagg acccaaatgt     900
gctaagaact atgaaaacat agaattaaaa gaatggggcc tggaataatt tacaacctag     960
taaagcagtt atgggaaaac atatttgcaa aaaaggtata caaagtataa tgaaataagt    1020
gtccagtaag gataaagtgc agagtaagtg aattaagcag cacccattca tgtgttcaaa    1080
ttcctgccag agtcaaaagg ttgtgctgaa gtagagtcca tgaaagcatc gtagatggct    1140
cctcctgctc aagttcccct gctctgcgtc ctgctactct ggccacaacc gtctggaccc    1200
agggttgaca cacaaacaaa cacaataatc ttttagccag acataaagaa ggccagccac    1260
```

```
caatcaggaa aattgtgtcc cataaaggcc cttcctattg aacagtgaat gacagacatg    1320
gccagatctt ctctcttgga atgctttgaa tgttagtcac agagagtgac cactagaagc    1380
acagatagca gtagaagcta agactacatg aaaaagcagt ggacagatgg tgatttatga    1440
gaatggcaaa attactagag tcataggcaa tggatacttg ttaatgaagg gatgagcagg    1500
gccccacagc ctgttgctgg ctcacaagtg cagttgattg ctggactgaa cagcagctct    1560
ccgcctgatg atagggtttt ttaaagtgtc cttattgcct taaagtaaat cctcagcatt    1620
tgcagtgctc tgagggtgtc ctagcatttt atacctttt tctaagagcc caggtaacat     1680
aagggtactc ctgttgttct ggctttaatt ctatctgcag aagagggttt cttgtgaaag    1740
aaagggtcag tatggtcttt tatctgtaca gcagataaaa agggtatgta cgtgcacacc    1800
tttgtacgtg gctgccttcc caggacagtc tgacagtaga gggtagaaac ttcagttgta    1860
gctgagagca ggcctggaat ccccatgctt atactttta tttcctcccc cctttcccat     1920
tgtgatcaca ggctacttca gtgtgcttgt ccttggagag agcaagggaa gggagagcca    1980
gggagactgt tcaagggagc caccaggctc gagaaagagg aaccccctgaa gacagtagaa   2040 agtgcaggtg ccaagaattt gaatatctac atcagagttt ctcaatgtgc acacagtgaa    2100
ctaccagttt aggatcattt gatttgctaa aaatgaagat tactggtcta ccttagacca    2160
actgaataaa atatctgggt gaggggccta ggaacttgca ttttttggtag gcatggcagg   2220 tgattcctaa agcatttacc cttgagacct ctatgttaag gaagaaagg taatgttgca     2280 aggaggtggt gccggcttct aagaaagtac ccaggactga acggcagaaa gacctgacat    2340
accatatgta taaattgctg tggaagtgaa aaggaaagaa aaagtgtctg aggtaaaact    2400
ggagtgtggg gtgcgtggaa caaatggttg gatgcagatt tgctttacga atcatgagcc    2460
tagatgataa ctgagaccat gtggatggat taggtttctg ctaatgccag aattttata     2520 atcagcataa aagtgctata taaagctttc ccctcttcta tattatagtc cttttaagat    2580
gtatggaaca tcaactatag gaagaacatc atattcacag ctgtaagagg aaacaagaac    2640
ttatcatgca cttgatgttg tacaaaataa atctgtgatt tatgcttgag tgaccacaaa    2700
gtagcataca cataagcgca aattcattca tttaagaatt ccttgtgtct attatgtacg    2760
agataagtat ctctgagctg cacggaatgt ggcttatcag aaggtgacct aagtttcaaa    2820
gcagattttg ttaagatgaa gacagagatt gacaggaggt ttaagacact ctgtctaaag    2880
taaagattta gagtcacaga gttcatggat taggatttag aatccacaga gggtccacag    2940
attcactcat tcaacattcc ataaatattt attgaatgcc tttttgtgtc agagactgtc    3000
ttaggtgctg gaaatttagc agtaaatgaa acagaccaaa acccatgccc tcatggagct    3060
tacattctga tggtagagag acaagaaaac aaaatagata gtgtattatt gaaggtgatg    3120
agagctctgg agaaaaagta ggaaaagaga cagatctggg acaagggcga aattacagta    3180
tcaaagatga tcttttagg gaagatctcc ttttaaaaac actttggaac aaagatttaa      3240
atgaggtgcc agagggtag caagtgcata ttccctgagg aagacgcctg cctggcattt      3300
tcaaggaaca gccagtaacc aatgtttatc tacgtaagta aggaagggag aacagtagga    3360
tgagagttca gagaagaggg tagggatat caaataattt aaggccatgt aggatttttg     3420
agaagaattt tgcttttatg tcaagtggaa tgagggccac tgatgatctg ggagtagagt    3480
gactatgatc cgacatgaag tatactccat tttttaacta tgtgaacttg tgccaacgtt    3540
ttaacctcta aatctgtttc gtcatttgta aaacggtaaa aagtatttta cctcataagg    3600
ttgtcgtgat gattaaataa gatgatacga taagtgcaaa agatttagct tgtacttaac    3660
```

```
atagagtagg cacattttct cccttccct gtctttcact tttctcttct gcccttcca    3720
cctggcgcta ggaggggag actggaataa accttgcaga ttacagcccg tgtaagagta    3780
gaaaggaaag gatgacagtt gatgtaaagc cttggttaac agacataata gctgggattt    3840
aaattcagct ttattggtgg tttatgatgt ggactagagg aatggaactg aaagtctcgg    3900
aggagggcg atcctatcag gtacaggcgc tgcttttcca gccctcaatc ctcaagactc    3960
tcccaagata catttctagg tagtttatca acacagactc cgggtatgct agcatgttta    4020
attgccccat tgtttaatgt cttaactcca cgaactttaa ctgattaatc tgtcttctaa    4080
ttaatgtttg aatgactctc ctcaggtcta aactaccaag gccatctcta cttaaaaaca    4140
gttgtctttt gtttgtgatt tcaggggccc tgggtataag cgaagtccct gtttagagac    4200
cttgtgatgg gttcaaaata tcaagaaaga tagcaaaata tcacaagcct cctgaccga    4260
gaagattagc gttgaaaggg tctgtcgtgt ttgtttgggc ctggggctaa attcccagcc    4320
caagtgctga ggctgataat aatcggggcg gcgatcagac agccccggtg tgggaaatcg    4380
tccgcccggt ctccctaagt ccccgaagtc gcctcccact tttggtgact gcttgtttat    4440
ttacatgcag tcaatgatag taaatggatg cgcgccagta taggccgacc ctgagggtgg    4500
cggggtgctc ttcgcagctt ctctgtggag accggtcagc ggggcggcgt ggccgctcgc    4560
ggcgtctccc tggtggcatc cgcacagccc gccgcggtcc ggtccgctc cgggtcagaa    4620
ttggcggctg cggggacagc cttgcggcta ggcaggggc gggccgccgc gtgggtccgg    4680
cagtccctcc tcccgccaag gcgccgccca gacccgctct ccagccggcc cggctcgcca    4740
ccctagaccg ccccagccac cccttcctcc gccggccgg ccccgctcc tccccgccg    4800
gcccggcccg gcccccctcct tctccccgcc ggcgctcgct gcctcccct cttccctctt    4860
cccacaccgc cctcagccgc tccctctcgt acgcccgtct gaagaagaat cgagcgcgga    4920
acgcatcgat agctctgccc tctgcggccg cccggcccg aactcatcgg tgtgctcgga    4980
gctcgatttt cctaggcggc ggccgcgcg gcggaggcag cagcggcggc ggcagtggcg    5040
gcggcgaagg tggcggcggc tcggccagta ctcccggccc ccgccatttc ggactgggag    5100
cgagcgcggc gcaggcactg aaggcggcgg cggggccaga ggctcagcgg ctcccaggtg    5160
cgggagagag gtacggagcg gaccacccct cctgggcccc tgcccgggtc ccgaccctct    5220
ttgccggcgc cgggcgggc cggcggcgag tgaatgaatt aggggtcccc ggaggggcgg    5280
gtgggggcg cgggcgcggg gtcggggcgg gctgggtgag aggggtctgc aggggggagg    5340
cgcgcggacg cggcggcgcg gggagtgagg aatgggcggt gcggggctga ggagggtgag    5400
gctggaggcg gtcgccgctg gtgctgcttc ctggacgggg aaccccttcc ttcctcctcc    5460
ccgagagccg cggctggagg cttctgggga gaaactcggg ccgggccggc tgcccctcgg    5520
agcggtgggg tgcggtggag gttactcccg cggcgcccg gcctcccctc ccctctccc    5580
cgctcccgca cctcttgcct ccctttccag cactcggctg cctcggtcca gccttccctg    5640
ctgcatttgg catctctagg acgaaggtat aaacttctcc ctcgagcgca ggctggacgg    5700
atagtggtcc ttttccgtgt gtagggatg tgtgagtaag aggggaggtc acgttttgga    5760
agagcatagg aaagtgctta gagaccactg tttgaggtta ttgtgttggg aaaaaatgc    5820
atctgcctcc gagttcctga atgctcccct cccccatgta tgggctgtga cattgctgtg    5880
gccacaaagg aggaggtgga ggtagagatg gtggaagaac aggtggccaa caccctacac    5940
gtagagcctg tgacctacag tgaaaaggaa aaagttaatc ccagatggtc tgttttgctt    6000
```

```
ggtcaagtta aacccgaaga aaacccgcag agcagaagca aggcttttc    cttgctagtt   6060
gagtgtagac agcaatagca aaaatagtac ttgaagttta atttacctgt tcttgtcctt     6120
tcccctattt cttatgtatt accctcatcc cctcgtctct tttatactac cctcattttg    6180
cagatgtgtt ctacatctca agagttatta cagtactcca aaacagcact tacatgattt    6240
tttaaactta cagaggaatt gtagcaatcc accagctaac cgcctgaaat agacttaaac    6300
atgtgcatct cctttttttt tttttttttg agacacagtc tcgctctgtt gcccaggctg    6360
gagtgcaatg gcgcggtatc ggctcactga aacctccgcc tcctgggttc aagcaattct    6420
cctgcctcag cctcccgagt agctgggact agtaggtgca cgccaccatg cccagctaat    6480
ttttgtattt ttagtagaga cagagtttca tcatgttggt caggatggtc tccatctgct    6540
ctgttgccca ggctggagtg cagtggcgcc gtctcggctc actgcaacct ctgcctcctg    6600
cattcaagca attctcctgc ctcagcctcc cgaataactg ggattacagg tgtctgctgc    6660
catgcccggc taattttttg tattttagt  agagacgggg gtttcaccat gttggtcagg    6720
ctggtctaga actcctgacc tcgtgatctg cccgcctcgg cctcccacag tggcatgtgc    6780
atcttatagc tgaagtctaa gccttcttaa atcttgagat ccatcaaaac agacaggttt    6840
tctaattgtt atacaatgta tatgttatgt ttataataga aatcatttta caaataagtt    6900
ataaatggga aaggtctatt tgtaattatc agctcagaat taaccataaa actggtgtca    6960
ctgaagtgac tgaggtccaa aatgctgact ctgcatgtta tagactacag atatcaaata    7020
tggttgctaa caatagttta ctttgagact gtagccatcc acagtatatt tgcttttaag    7080
agatggtaga tggtaattca gttttatgaa aaataaaaat gaattttctt ccattacaaa    7140
attgttggat tcgagtccag tccactcctt actagctttt ctaactctcg gtgagggatc    7200
ccctcccagc ccatgatctt catttggtaa gactcctttg gaacccagtt ctctctagtg    7260
gatttaaatg tgatttggtt ttaaaaatct cattcaagga attttttttt tttctggaaa    7320
caaccaccgc ataaacaagt aaaccggaag atacatgtgg ctctgaattc atatatatac    7380
acaaactcta atccaatgtc tgtccacagt atttcctagg ctagtaaact ttttggcctt    7440
aacgacccct ctaccctctt tgtttttttg agagagagag tctcactctg tcacccaggc    7500
cggaatgcag tggcgcgatc tcggcccgct actacctccg actctcaggc tcaagcgatt    7560
ctcccgcctc agcttcccga gtagccggga ttacaggctc cgccaccgg  gctaattgta    7620
tttttagata cgggatttca ccatgttggc caggctggtc tcgacctcct gacctcaggt    7680
gatccgcccg cctaagcctc ccaaagtgct gggattacag gccaccacac ccggcctaca    7740
ctcttaaaaa ttatcgaagg ggccgggcac attggctctt atctgtaatc ccagcacttt    7800
gggagactga ggcgggagga tcgcttgagg ccaggagttg gagaccagcg tactcaacat    7860
agtgagacct tgttataaag aaaaaaaaaa tccaggatta aaaaaatct  ttgatttgtt    7920
tgggatttat taatatttac cgtattggaa attaaaacaa ttttttaaaa tgtattcatt    7980
taaaaataat aagcccatta cttggtaaca tgaataaaat attttatgaa aaataactat    8040
tttccaaaac aaaaccaaaa cttagaaaag tggtattgtt tcacacttca gtaaatctct    8100
ttaatgatgt ggcttaatag aagatatgga ttcttatatc tgcatctgca ttcaatctat    8160
tatgatcaca catctggaaa acttgtgaaa gaatgggagt taaagggta  aaggacatct    8220
taatgttatt atgaaaacag ttttgacctc ttgcacacca gaaagtcttt agtaacctga    8280
ggggttccta gaccacattt tgagaactgt ttaggctat  gcaaactggt tggggggagg    8340
ttggggtagg cagagagcta gaagatacat tttagtgtaa ttctcctcat ctattcctaa    8400
```

| | |
|---|---|
| ttgctttggc ctacatttga aataaagcgt ggaggcaaac gggataagat acatgtttgt | 8460 |
| agtggttgtt aacttcaccc tagacaagca gccaataagt ctaggtagag cagagtaagg | 8520 |
| cggggaacta tgccgtgacc gtgtgtgata caattttttct agcctgtggt gcttttttgcg | 8580 |
| gcagggctta ggagtaaggt tagtatgtta tcatttggga aaccaaatta ttattttggg | 8640 |
| tcttcagtca attatgatgc tgtgtatatt tagtgtttat ctacaatata tgcacattca | 8700 |
| ttaatttgga gctactcatc ctataataaa tagttgtgca tttactccca ttttttttctg | 8760 |
| catttctctc cttatttata attatgtgtt acatgaggga aaggaggtga aattaaacat | 8820 |
| tcatattatt tcaaaaaatt tgaaacaact aactaaaaaa tatgttttat tttctgtatg | 8880 |
| gtgtttgtta tacaatctgt caatattcat gcacctcttg ggagacagtg tatgaaaagc | 8940 |
| aaagagtaac agtcacatgg attactgatt actgagatat attcacttgc atctttttttt | 9000 |
| ttttttgaga cggagtggct ctgtcgccca ggctggagtg cagtggcgtg atctcggctc | 9060 |
| actgcaagct ccgcctcctg ggttcacgcc attcttctgc ctcagcctcc caagtagctg | 9120 |
| ggactacagg cgcccgccac cacgcccggc taattttttttt atatttttag tagagacggg | 9180 |
| gtttcaccgg gttagccagg atggtcttga tctcctgacc tcgtgatcca ccctcctcgg | 9240 |
| cctcccaaag tgctaggatt ataggcgtga gccaccgtgc ccggctcact tgcatctctt | 9300 |
| aacagctgtt ttcttactaa aaacagtgtt tatctctaat cttttttgttt gtttgttttgt | 9360 |
| tttgagatgg agtcttactc cgtcacccaa tctggagtgc agtggcgtga tctgggctca | 9420 |
| ctgcaacctc tgcctcccgg gttcaagtga ttctccttcc tcagcctccc cagtagctag | 9480 |
| gactacagga gagcgccacc acgcctgatt aattttttgta ttttttagtag agagagggtt | 9540 |
| tcaccatatt ggccaggctg gtcttgaact cctggcctca ggtgatccac ccgccttggc | 9600 |
| ctctgaaagt gctgggatta caggcatgag ccgccgcacc cggcttttcta atctttatct | 9660 |
| ttttttgtgc agcggtgata caggattatg tattgtactg aacagttaat tcggagttct | 9720 |
| cttggttttt agctttattt tccccagaga ttttttttttt tttttttttt tttgagacgg | 9780 |
| agtcttgctc tatcgccagg ctggagtgca gtggcgccat ctcggctcat tgcaacctcg | 9840 |
| gactcctatt ttccccagag atatttcaca cattaaaatg tcgtcaaata ttgttcttct | 9900 |
| ttgcctcagt gtttaaattt ttatttcccc atgacacaat ccagctttat ttgacactca | 9960 |
| ttctctcaac tctcatctga ttcttactgt taatatttat ccaagagaac tactgccatg | 10020 |
| atgctttaaa agttttttctg tagctgttgc atattgactt ctaacactta gaggtggggg | 10080 |
| tccactagga aaactgtaac aataagagtg gagatagctg tcagcaactt ttgtgagggt | 10140 |
| gtgctacagg gtgtagagca ctgtgaagtc tctacatgag tgaagtcatg atatgatcct | 10200 |
| ttgagagcct ttagccgccg cagaacagca gtctggctat ttagatagaa caacttgatt | 10260 |
| ttaagataaa agaactgtct atgtagcatt tatgcatttt tcttaagcgt cgatggagga | 10320 |
| gtttgtaaat gaagtacagt tcattacgat acacgtctgc agtcaactgg aattttcatg | 10380 |
| attgaatttt gtaaggtatt ttgaaataat ttttcatata aaggtgagtt tgtattaaaa | 10440 |
| ggtactggtg gagtatttga tagtgtatta accttatgtg tgacatgttc taatatagtc | 10500 |
| acattttcat tatttttatt ataaggcctg ctgaaaatga ctgaatataa acttgtggta | 10560 |
| gttggagctg gtggcgtagg caagagtgcc ttgacgatac agctaattca gaatcatttt | 10620 |
| gtggacgaat atgatccaac aatagaggta aatcttgttt taatatgcat attactggtg | 10680 |
| caggaccatt ctttgataca gataaaggtt tctctgacca ttttcatgag tacttattac | 10740 |

```
aagataatta tgctgaaagt taagttatct gaaatgtacc ttgggtttca agttatatgt   10800
aaccattaat atgggaactt tactttcctt gggagtatgt cagggtccat gatgttcact   10860
ctctgtgcat tttgattgga agtgtatttc agagtttcgt gagagggtag aaatttgtat   10920
cctatctgga cctaaaagac aatctttta ttgtaacttt tatttttatg ggtttcttgg    10980
tattgtgaca tcatatgtaa aggttagatt taattgtact agtgaaatat aattgtttga   11040
tggttgattt ttttaaactt catcagcagt attttcctat cttcttctca acattagaga   11100
acctacaact accggataaa ttttacaaaa tgaattattt gcctaaggtg tggtttatat   11160
aaaggtacta ttaccaactt tacctttgct ttgttgtcat ttttaaattt actcaaggaa   11220
atactaggat ttaaaaaaaa attccttgag taaatttaaa ttgttatcat gttttttgagg  11280 attattttca gattttttta gtttaatgaa aatttaccaa agtaaagacc agcagcagaa   11340
tgataagtaa agacctgtaa gacaccttga aggtcatgga gtagaacttc catcccaagc   11400
agatgaggat ttatttaatc tcaaagacct ccaggagggg acattcccca actgtccttg   11460
ttaactcatt tcagaacat atttattagc atattttaca tgtaatttgg atcttcatgt    11520
taaatttaac atcagtggag atggaaaata agcatatcgc cttgtctttg aaatagccct   11580
atattgttag attgtttctt aggcttcttt accctgggtt aagcagtcct aatactttag   11640 cattattct acatctagtg tactaattta aaaaaatcag ttctgaaaaa tttctaagaa    11700
ctttcttcaa gttccaagct gtgaaatcta aacaggtca aagtgccta ttaacgtact     11760 gtactgtgta gtgtcttgaa gagacacttt gcgctgaggc aagttctgag ggcattgggt   11820
ggccttggga agatatttat gcagtttaga acctggagaa ttgattagat aactaatcat   11880
aaggaaacgt cacatatttt tggtactata aaaagtgga gaaataatgc ctatttgcaa    11940
agatttgatt taaacataga aacaacttta tttggcttcc aatttaaga atttacagca    12000 gtaaagggga acagtctaat tgaagtagac tgcctatgca atagtctctg tatatttact   12060
tttgacaagt taattcaatg tgtactatag ttttgtttct ttgaagaggt ttgaatagtg   12120
cacccatttt aatctgtatt gcaaattcag ggttacttgg cagactctac tatttaaatc   12180
agatgtaaaa ggaagtttta atataattca ctttatgcct gaaagttttc ctgggatttt   12240
ggaaggtgat tttactggaa atgctgtctg tcttccctga aaatctgaga aattccatta   12300
cactttgttt ccaatcagag gtcatgagtg ctatatgagt atatacagca tgacgtcatg   12360
aatgtgataa agtgggttag gaaacctttt gctaatgatt gttaaaatgc aatataaatg   12420
ttgaagaaat aaagctaaca gttaagcctt tatttgggcg gaaggctgaa aaagtttata   12480
aacttaaacc tataactctg cttatgattt ctgccaaacc agaagacttg actctgggaa   12540
gcattggtta cctgtgaact ttgaaactga cggtccctga cgtagtttag tcacctggga   12600
aaaggtatct gagattatct cttatctccc aagttacagt gagtctctga gggaactgac   12660
acattacatt aagttcttgg tgtagttaaa ctgtaagaaa ggcaggagaa cttagtagtt   12720
aaatagttgg ttaaatggaa atgctgactc catgttattg taaaaagtta aaaatttagg   12780
aggatatggg gatttcactg ccattgcagg ttttgattgg tatttaccaa tccgtgtggg   12840
tcagagagaa aattagaaag gatatgactg cacatttttgg aattattagc agttttttcta  12900 catttaaaat ggaaataaat ttttaaaaa tttaaatcaa gtaatactgt attttttggt    12960
gatttagatt tttcaaaatt tacactaaga gatagtaagg agggtggcta ttgtttcttt   13020
caataatgtc tctgagaggt tgtaactcat ctaaggatac gtagctaata agtggtagga   13080
tttcaattta aattctctga gaccaagtta agtagaattt gcactgtact cttgtataac   13140
```

```
tttttaaaac tgaaaattag ctatctttca aattaagaaa atatttacta atggagacta    13200
attcagattt gtaagtatac caaaatttga acttagcctg ctatctaatg gcaacttagt    13260
ggcagaggta tgatgtaaaa tcattcaggt atgacacata gatggagtat gtttgtattc    13320
gaggctgtgc acataatcac ctttacttgt attgtgaagt atatattgtt atcttttatg    13380
aagcccacta aagagataat gaaataccte gttattaggg caagattatt gaaaactcaa    13440
aatagcccce aaacacaata cttggctaga aatatatacc tttatagttc agagatcatt    13500
tattatcaaa accctgaagt ttttttttcta aggtaaaatt tggtggaaga ggaaaagtct    13560
cgttttaaaa aaatgtaggt agttacagag atcagaatga ttagttgatc acttaccaaa    13620
tatatattaa gtatctactg tatataatat gctagtaaga ataaatatag caggaagtat    13680
tttttcccag gctctaattg tttgacatca gcatgctttt attgtggcac ttataattca    13740
gttcaagtat tatgcccctc tttgatggaa cagtttccta ttcagtaagg aagaccagat    13800
taatcattgg attggtttgt ttcatcttta gtgttctgag ctgtagagta tttatttacc    13860
aaggtttatt ttaatttta ttttattttt attttccat gttcattgta gaattcattt    13920
tacctacgaa tgaagtatgt agattataga gagaaattt gtaaaattaa actgatactg    13980
aagactggta taagaaaagc cttatgtaat ttgtaagctg ctattcttct gagtttatac    14040
atatatcttt agtaatcaat gagggatggt tgggtgactg ccctccaggg gacatttggc    14100
aacatctgga gatgttttttg gttgccacaa cttggggaga gagtactgct actggcatct    14160
attgagtaga tgctattact ttaaatggca aagctgcagt tacctttgca ccaacctaat    14220
attaaacttc ctgcagtgca cgggaaagcc cccacaacag ggttatctga ccccaaacct    14280
caatggtgtt aagatccaaa ccttgatatg ttaacctgta gctttaaaca tcctttaaat    14340
tgtcaaattc atgtccctga cataaggttt atgttagatt ttcaagtata acaaagattt    14400
aaactttaac ttttgtacgt taatgatatg ttagcttact ccagtcttct attaaaacat    14460
tctgtttta aaatcagaga cacacagcaa ttttataaat catttctctt caaggctgtg    14520
aagctctccc cacttttgtg agtgccctct actggtcaaa ttatttgctt tataacaagt    14580
aacagtgaaa tcctaagttt gtgtagtttc gctgttaaa ttatgggtgg catcaattta    14640
taaatatatt cgttttattt aaaagtctta tatgattgat ttcgtatcat ttttgctctc    14700
tgctaatatt aatataaaga ttactgtctg tattagttag gcctaactaa gtaggtgagt    14760
atagtgaact aagaaaggaa acgaggcagt atataagaaa ataggggtggt tcagttgtta    14820
acacttactg agcttacttt gttgaaggga ctaaaaggca gcagtgtggc tctctgagct    14880
tctttgcatg cactcaggag ctgcttaatg gagtccaagg cttggtggtg tgttacaggg    14940
gatgatagga gggtcctatt cagaagtggc aaattgtgaa agtgcacatt ttgtagagtt    15000
ttataggact gtagaatagt tgtgagcacc tgatttttag aataaacaga aaactcaggt    15060
actgtattta ggtcaaatta agaataagta tttattaaga cctgaatata aactttact    15120
ggtcatggtt tttttctacc ttgggttttt ataaatccaa agatttaaaa acatacaaat    15180
ggaagttggt aatggaatta agtgaaagga aaaatgatt ttatggtttg gaatctccta    15240
agattctggt tttaacaata caactaattc cttaatccta gaaatgttct tcactgccca    15300
ctttgtacca tgcagtcttc ctgtgggcta gagatacact gaggcgcaaa acagaccaga    15360
ttcctgcctt catggagctt attagtttta ggtatctcta gatttcttgt aatacctatt    15420
acaatgcctg cacatcagtt cattcatgtg ggttcaacgt agtactcagt acatggcaaa    15480
```

```
ttcaagtttt acttttcgga acttcatgga ttttttttcct cagaatatct tttatccata   15540
attggttgaa tctgtagatg cagtacccat ggatatggat ggcccacttt attttgaaga   15600
gcagtgtttc taggcaatca tgctaattat atatgactta atttagaggc tttatactta   15660
agagcattac atttctggcg tctcttaacc attattattt cataatgtgt aggttatgga   15720
acagttaaat tattgggatc ttaatataga aattagtaga aataagccag atatggtggc   15780
tcatgcctgt aatcttagca ctttgggagg ctgaggctat cgctgtact attttttact   15840
acttttctat aggtttgaaa ttttttcaaa ataaacatt gaaaaagta aggtaggtag    15900
tgtgtccctc cttaatcctt tcaaatattt tattttcact atttctatta attttttttt   15960
ttgttttga gatggagtct cgctctgttg cccaggctgg agtgcagtgg cgcgatcttg    16020
gctcactgca gcctccacct cctgggttcc agccattctc ctgcctcagc ctcctgggta   16080
gctggtatta caggcatgca ccaccacacc caattacttt ttgtattttt agtagagacg   16140
gggtttcacc atgttggcca ggctagtctc gaactcctga cctcgtgatc tgcccgcctc   16200
agcagtgtca ctgcttctag accgttttca aggcacagag cttagaaatg catgttacta   16260
agaaatcaag agttaactat ttttcacctt cttctcccg cagtgagaac cctggttcta    16320
ccctgtttct cctgtgtaa attttaatgc taaactatac acttgtgaaa taaaaatgat    16380
aatgtcattc ttaaattatg gatcttgcag tgttatctaa gtaacataga ttgagtgatt   16440
taactttagg tttccttatt tgtggaattt ggataaaatat ttttcaccct tgagaaaagt   16500
gagactcctt tctcatcatc agagtatcct taaccatta aggcaaacat ttgggaaaaa    16560
actgagctat ctggctgcat aaaaattaag ttttctttaa caagataga agacaaatga    16620
aaacctagaa aaaccatttg gttcaagtaa caggaagcta tcttatatat gaattagaga   16680
aaagcaaaca cacaaataga aaaaaaggga tgggggtac taaagatata aatagcttgt    16740
ctaccaaaaa agaaataaaa taaataacat gaacatataa aaagacactt acttcatgaa   16800
tgtgatgcaa gttcaaacaa taaataacat ttctgtactt tcatattggc taaggttaaa   16860
atgataactg ctaggaaggg tatggagaag tgtgcgcctt gcactgtagt gggagtatag   16920
accctcagac tttatggagg tcagtctgga aatatgtttc aaaatgtaaa ctacatgtcc   16980
tttgaccagg taattcaact tcttgaaatt tatccaagga tttaattgga taaatgttta   17040
agatgtatat ataagaatgt ttactgcagt gttgttatg attttaaaaa aatgaaatc     17100
atcttcatgt ctaccaatag agaatgggtg aataaattat ggtatgtcca tatatacaaa   17160
ttacatagtt gttggaaata ttaggtagat ttagatatac tgatgttcaa aaatgtccat   17220
tatgtaagtg aagctgggtc acagcacctt gtgttgagta tgatttcatc tagaaacaaa   17280
attactccct catcctttgt tgtgttttag ttttttaaaa taagcttata ccattgggct   17340
gggggaaaag taaatactcg ttttggagag agaaaagggc actaaagttt cagataccgt    17400
tagattattt catgcttatt tttcaagcct caataaatta cataattcac atgtagtctt   17460
ggattaagga aattgctatt aaggctaaat aaataatatg agaggtatat aatataaaat   17520
atgaacatta tattggcatt aagattggat ccacggtcat tccagcctct cattcttacc    17580
tggacttcaa gtgatcactt gtgggcaaat gccatctgac ttgaacaggt tacacatgta   17640
tgctcattat atcgttattt tcaaaatttg tcatataaat tttccttgag ttcattcaga   17700
tttttgaact agtttttct cttgggagta gtacacactt aattctctct agtactaagc    17760
taatgttcac cattccttata atttaagta tccagcattt agtaaagaag tctttgtttt    17820
ctttatcctt acttttagtg aatgtcttag ttttaattg aaaattctgc catgaaaata    17880
```

```
agctctttaa catcttcact ccctaatcaa aacagaaatc cttcatagcc ttcagttgta   17940
gctatccttc cctgtgattt gtccagctcc attatattta ttttgaaata tggtgaccag   18000
ttttgcaaaa ttatttcaac tgtaggtgcc cagtgatttt gtaaggagaa gatactgttt   18060
ctgaacagtt ctcagtagcc agtggcctgc ccctactttt tggcctgcgt gtagtatata   18120
aaataatgca gttaactttt tatagcactt ttcattttat aaagagattt tcatggtctt   18180
taatattaat ctatgtataa agtcctgtat gcagttttac ctactttcac agctgaagga   18240
acaatagctt agagaagatg tgagataaag tagtttgccc aagcccatag cacaaataag   18300
tgaagttctt cggctgtcca tggatcgaag actcccaagt ctatctctag cctggacttc   18360
tgtcctgagc accagacatg tatgtatatc aagatgcctg caggtcatat ccaccaggac   18420
aacccatgag tacagggaat tcaacatgcc caatatcact catcttttcc ttcgccctcc   18480
cctttgtact catcccctgt cggtaagctc tgttatttta aaaaattgaa atgtattcac   18540
atagcataca atttacactt ttcaagtgta catggttttt agtatattca caagggttgt   18600
gcagtcatta ctactaattc cagaatgtta ttatcacccc aaaagtccca catccattag   18660
cagccactcc ccaatccctt ctcccaccag cctctaaaaa ctgctaattt ttccatctct   18720
gtggatttgt ccactctgat tatttcatat aaagagaatc gtacagacgt ggccttttgt   18780
gtctggcatc ctccacacag gatgatattt tcagagttcg tctatgtttt tgcttgttga   18840
tcattccttc attcctttt ctggctgaat aatactctgt tatatggata taccttattt   18900
tgtttatctg ttcatttgat gggcatttga gtgattccct cttttttggca attttgaata   18960 atgccactat aaacatttat gtacacgttt ttgtgtgacc atatgttttc acttctctcg   19020
ggtgtatatc taaggtacag ttgctgggtt atatggtagc tctgtctttg acttttttgag   19080 gaactgccaa gtggttttgg tagtgattgt actgtttaca ttcctaccaa caattttacc   19140
taagtatttc tcaaatctat ttaatctttt cggtccatac tgctgttgct gccttagttc   19200
agattttgtc atttcttgta ataattcgta gctcatctcc cagtctctgc tcccctctct   19260
ccctccctcc cccttcttct ctctcttatt tccacccatt tttaacattt atagaagtca   19320
aaagtctagt tcagaaagca gaaaccatac tagatatttc agcacagaga actaattagg   19380
tgttggaaga ctgaaaggca aaaaaacact gaagtaacac agtaacatca agaatgggca   19440
ctactcctaa gattcaggga atgctgggaa gatttggggt ttatcagaac tggaagctca   19500
gaggaggggc cccttgtcgc tgaggcttaa tccctgcaga ggtgcctttg gctgctactg   19560
gtgaatctga gtgggtatga tgagtcagtg tctgggaagg gccaaaacat tttgtccctt   19620
tctataattt gtcatgataa tgctagtaat gaatctgatc tcccttccta ttttaaaaac   19680
cttttagtga ttttgtatag gatgaagttt aaaactcctt acttaatata cacatgaccc   19740
tccgtaagct ggcccctgct tgattgtcca gtttcacttc ttggtgctta ttctaaggcc   19800
tctaagcctt agagatcctc taagcctttg agatccccaa accctggact gcggactggt   19860
acccacctgt gtggcctgtg aggaactggg ctgcacagcc ggaaggaggt gagcattact   19920
tgccttagct cctgtcagat cggcagcatt agattctaat aggagcgtga accgtgttgt   19980
gaactgccca tgcaaggatc taggttgcat actccttagg agaatctaac taatgcttga   20040
tggtctgagg tgaaacagtt tcatcctgaa atcacccca actcggtcct tggaaaaatt   20100
gtcttccacg aaactggtcc ctgatgccgg aaaagtgggg gaccgctgtt ctaagctaaa   20160
gttatatgga gctccttggt tctgtgtcct caacatgctg ttctatgttt tttacattct   20220
```

```
gtttgctcct tcctgcttgg aatgtccttc ccctccccgt ctttcttaat gcatacaaag   20280
ttgatctctc ctgtgtgcca ccattgtact tcgtcttgca tatggtgtta cattcatttt   20340
attttaatta tttatttacg ttcatgtctc ttccactcac cttagttgct tgaggtcaga   20400
aactatataa tgtgtgacac ggaatgtgac acctagattt tcaataagtg tttctatgat   20460
acaagggaga ctgatgtggg tagatgggaa tgaactcatc aacctctgtt tacataccct   20520
aaattccctg tttcttccct attataattc tgacagtcta caaccgtctt tgatggctta   20580
taaacggaaa gtgcggaaca catcattcta cagtgaattt aaataacctt tcggaagagt   20640
aacgtaaagt acttgagcat taattgagta aaagtttctc atcttttcct acaggtgtta   20700
ttaagcagta tgtaaaaagt ccttacaata cttaatacat taagaaaaca tacaatttca   20760
agaggaaatc cccgagtaat acattattga cattttcagc agttctagtt atattgagaa   20820
gagcatctca tggaattggc agaatgaaga tggagattaa atgagatgat gtttgtaata   20880
tgcttatgac agtatctggc atataagtaa gggctcagta aatgttgact gctgtaatta   20940
ctattaatag taatatgatt accttttagta aaagttatta gtttctttag gttttttgtt   21000
tactacaata tagtaaacaa atctatact tggaatgtat atattgtttt gtttgatac   21060 atggaatatg tctctgtgtc agagtcactg cctgagttgg aaaacccata ctcgagtatg   21120
ttaaaaggtg aacacactga ataatttagt tattaattat aatggaaaaa tgacaaactt   21180
gatgttctgg ttaatgaggt tatcttatct tgaatgagtt agcttttaaa ttcctcaaaa   21240
taaaggcatt aataaaacca ggaaacactt cattaaaaaa attatgcaag tcagtgtaaa   21300
agaagattaa aattccacat gggcaaagga cacacgttgg cgataaatat gcagataaga   21360
aaaaaaacct atataacatt attactcctc aaagaaattg gtatgaaaac aataaaaatg   21420
tgtagcttat caaaccaaca aaaatttaaa aatatgaaat ccattttaag taatgataaa   21480
atgggtgcac tcttagtgct ttatagaata gtagtataat gaacctcatg tgtgtaccaa   21540
ccagctcttt catatcttaa catttagcaa catttgattt agctctttct tttttccaag   21600
atagaaaagt taatattgtt gaagactcct gcattctttt ccctagtctt attttcttcc   21660
ctcccataaa tgtgttaaaa tctctgtgtg tattgttttg gttgtatttt tacataaaac   21720
tttacatatt atataaaatt taattgaagg taaaatttat taaattattc ttaatatata   21780 ttgtaatttta aaaattaaca gcttcattgt cttgataaaa tttatggtat cttaaacatg   21840
tgcttgtttt tctaagagaa cattgaaaca tagatttaa aacaaattgt tgaaagatta   21900
aaaaatctgc ctttgcacac tgttacattg aaagtgggc atttgtcgtg aacattcatt   21960
tcaaatatgt agtatcttca gaatatttga gaaggatttg tattatataa ttgaaaaatc   22020
tgttaaattg tatttatgtt aactgcttaa ttctaataaa atttccattc attttttagt   22080
atctgcatat atttacatca aatggattca ttcacttatt taagaggcag tactaattac   22140
ctatagcgtt caagactgtt aggtagaggg tgtgtagtgg tgagtacaac aggcgtgagc   22200
cctaccaaca cggagtttaa agcctagtag aggatatanga cttaaacaat tcacaagta   22260 aatacataat tacaaattat aatacatgct atgaaggaaa cataggaggt accagagaag   22320
gaagagtgct ttgcatttt atttttaaga ccgaagagtg ctattggagg actttgagca   22380
agtgaatgac atgatctaac ctaccttcgt tcattcattc attcattcat tttcttcctt   22440
cctggctcaa gcagtcctcc cacctgagct ccccaaatag ctgggactac aggtacacac   22500
taccacacct aatttttttt tgtatttttt gtattttga tgggatttta ccatgttggc   22560
caggctggtc ttgaactctt gacctcaggt gatccacctg tctcggcctc ccaaggtgtt   22620
```

```
gggattatag gtgcctagcc catggtgcct agccctaacc tacatttata aactatcact   22680
tgctgctgtg tggagactat attgtgagat aacagcagg gatacctgct aggaagcaat    22740
tgctgcagat tgcctgagac aaaatagtta tcatggacta gggggatggt ggtggtggtg   22800
gtggtaggtg gttggatgta ggatatattt tgaagatagg taaatggtgc aagattatgg   22860
gtcagtttta aatgcttaag taaattttct ttgtaagaca ttttaggatg ccatgttaag   22920
aatctcttta taactgtcat ttaaaaaaaa accacatatt ttcttagcat aatttcccat   22980
agtaacatta ctatgtcaaa ggctatgaac atttgaatga ctttagataa atactgtaat   23040
tgctttccaa aaatattgtg cttattatgt caccagaaat gtttgaattc tgtctacaat   23100
tcagtcttgc cagtatagta catttcattt agaaaaattt tttactatgt agatggaaaa   23160
aataatattt tagctgggag tgggggggact atggggaata acttccttc atttaatatt    23220 ttattgtgag ttagtttaag ttactttatt ttatcgtagt ttcctaaggc tacaaattag   23280
taaccttggt aacttatgta cctaatttaa aagtttactt ttttgaaagg ctggaaatac   23340
taattaaaaa cgtaacacct tcatccttgt ctttgctcca ttattaacta gtttcattac   23400
agaatctctg tgttttaaaa tcagatgggt tttcataacc agtactttct cagagtggta   23460
aatttaaaaa aatatataaa gagaataaat aatatttgtt gagaatactt caaataatgt   23520
gaagagttat taacttacag caggagttgg caaacttttc tataaagggc catatgggtc   23580
tttgtcacaa agtcttgggt ttttgttttt gttttttaa acagctattt aactattcct    23640
agctaatggg caatacaaaa acagtgggca agatttggcc tgtgggcagt agcttgctga   23700
aaccttattt agactctaaa ttttttgaaa gagtctacat tgatgcatat ttttttttct   23760
tcctccaaat acagttgacc cttgaacaac atgcgtttga gtgaccatgg gtccacttgt   23820
gatacacgtt ttttttcccaa ccaaatgcag atatggaggg ctgacttttc atatacctgg   23880
atgttcctgg gccaactgta ggactagagg ctgggggggt cttggaacca atgccgtgtg   23940
tataccaggg atgactgttt cttatggcct gacctgaagt tggaacagaa tctttattaa   24000
tatataattt ttgttgcgtt tgttttctct ttatatttat ccattctttt tagatcgtat   24060
ttcatttaac acttttctt ctttagttttt taccaagttg cactgaaaat agctcagtga    24120
ctaattgcac ttctaagagt gaggaccccta gttaaaatta actctaaaaa tactgaattt   24180
ttaacctaaa cctttattt ctaatcaaca gtattattta tgagtaggtt atagattact    24240
ttgaaacgga atgtgtctca gaactttgct atcgatattt ttaaggtctg gtagggaaaa   24300
gataatagga atgagattta tcagtgaata ggggactgct ttcccagttt ctcggtcgca   24360
ctggtgtatt caccatggaa gcatcttatg aaatatgtac ataaactact aatatcccac   24420
attacaggtt gactattctt tatctgaaat gcttaggacc tagaagtatt tttggatttt   24480 ggttttttcag agtagggata ctcagcctac attggtaagt aaagaatgtg aggtgacagg   24540
ctgggcgcga tggttgacgc ctgtaatccc agcactttgg gaggccgagg cggatcacct   24600
gaggtcagga gttgaagacc agcctggcca atctgtacta aaaatacaaa aattagctgg   24660
acacagtggc acgtgccagt agtcccagct actcaggagg ctgaggtagg agaatcgctt   24720
gaacctggga ggcggaggtt gcagtgactc gagatcgtgt cactgccctc cagcctaggc   24780
aacagagcaa gactccatct caaaaaaaaa aaaaaaaaa aaaaaaaga atgtgaggtg     24840 gcagcaatag gtaggaagag tctttggtca gctttacatg ctctgtagcc atgcctgggt   24900
aatgggttga ctctaagact ctgtgctttg ctcccacctc ctgcttttc attactcttt    24960
```

```
agaatggttt ttaatttgtg atctatagga gttctttcaa gtatttaata agagaatagg    25020
ctaaattaag taaatgtcaa ctgaatgctc aaatctctac taaagagcct cttatttaga    25080
aaataaatat ccatcttttt tttctgactg gtgagataat taattttttat tacagatggt    25140 ttggaaaata ccatatgctt taaaagataa gcacaaaatt atagtctaat atgtaggttt    25200
tcatacttta aaaaattgaa aaccaaagaa aaacatttaa catagcatct agtacaaaga    25260
aaagagataa gcaagagata aatgtctttt ttgggacaga gttttgctgt tgttgcccag    25320
gctggagtgc aatggcacaa tctcagctca ccgtaacctc cacctcccgg gttcaagtga    25380
ttctcctgcc tcagcctccc gagtagctgg gattacagtc atgcaccacc aggcccaggt    25440
aattttgtat gtttagtaga gatggggttt ctccgtgttg gtcaggctga tctcaaactc    25500
ccgacctcag gtgatctgcc caccttggcc tcccaaagtg ctgggattac agacatgagc    25560
catcgcaccc ggccaagata aatgtctttt aaattatctc cattaaagac ataacctttta    25620 taacattttg atgtatatat taccagtttt taaacacata gtagatttgt ataaatacat    25680
aaacacatat tattgtgatc atgctgcact tagacatctt tatattctcc ttatactgta    25740
aacattttga aatactttac taacaacatt tgtaatgacc attcttttctc tctttctccc    25800 tctgatagaa tggtctacag agtaattcat aaactaaaca tactttagag gctgggcgca    25860
gtggctcatg cctgtaatcc cagcactttg agaggctgag gcgtgcagat cacgaggtca    25920
ggagttagag accagcctga ctaacatggt gaaacccccat ctctactaaa aaacagtac    25980 aaaaattagc cgggcgtggt ggcgtgcacc tagaatccca gctactcaag aggctgaggc    26040
aggagaatca ctcgagccca ggaggcagag gttgtagtga gccgagattg caccacagca    26100
ctccagcctg ggcgacagag cgagactcca tctcaaaaaa aaaaaaaaaa gatacattaa    26160
tactatagcc tacatgtgga acattaagaa aataattgct tttatgttta tgctttatac    26220
ctgttgttag ccctgcttct tatttcatga tttcatggct tcacattgta acatcccttt    26280
accatatttt ttgaggactg ttttggcaga atgtgtgaaa tcttgagcag aagtattacc    26340
caaaagtcag aagaaaatca gattttttatt tcaagattct gttaaagtta cccactccct    26400
tcttttactt aatcttatag ttgcagttct ctctcttttt agaaaagaaa aaagaggccc    26460
ctcaggattt gcagatgaaa caatattgct ctttagagat atccatctgg ctgttagatt    26520 attttttccac agttttcaga agtggatgag gccattagaa tcttgagtat tgcccatttc    26580
cttatgtgtg cctttgacta tagataaaat agatgcatga caattattta taagttgatt    26640 gattttttctt gtcatttaaa tcatcttgaa taatagagtt ggtagagcta tcccattttt    26700
gaaattattt tgttttgtca ataactttt gttaccagca tgtacacttg cattgttgac    26760
tctccatata ataccttaa aaaattttt tttgtggtaa aatatgcata acataaagtt    26820
taccatggta gttttctttc atttgttttg ttttttgtttt tttgagacgg agccttgctc    26880
tgttgccagg ctggagtgca gtggagcgat cttggctcac tgcaacctcc gcctcccggg    26940
ttcaagcaat tcccctgcct cagcctcctg agtagctggg actacaggcg cccgccacca    27000
cgcccggcta atattttgta ttttaataga gatggggttt caccatgttg gccaggatgt    27060
tcttgatctc ctgacctcat gatccgccca cctcggcctc ccaaagtgtt gggattgcaa    27120
gtgtgagcca ccgcgcctag accatggtag ttaattttaa gtgttcaatt cagtgacctt    27180
aagtgtgttc ataatgttgt gcaaccatca ccatgttgtc taaccattag cactatctgt    27240
tttgagaact ttttttatc atcccaaatt agaattctgt acctgtcaaa tagtccccag    27300
taatcctccc tcccccagcc cctggtaatc tgtagtctac ttttcgtctt tttgaatttg    27360
```

```
cctattttag gttcctcata taagtggaat tatgtggtat ttgtcctttt gtgttggctt    27420 actt catttta gcataatgtt ttcaaggttc atctgtgttg tagcatgtat atacaggttg   27480
aagcatccgt tatccaaaat ggttgtgacc agaagtggtt tggatttcag atttttttt     27540 tggattttgg aatattcata gatacttaac tggttcagca tccctcgtcc aaaaatccaa    27600
aatcagatgg agctcagtgg ctcatgcttg taatcccaac acgttgggtg gccaaggcag    27660
gaggatcgct tgagcccagg agttcaacca gcctgagcaa cacaagaccc tatctctcca    27720
aaaaaaaaaa aaaaaaaaa aagatgaaag aaaaaaaaat ccaaaatcaa atgctccagt    27780
gagcatttcc ttttagcatc atgtcaggct ctaaaagtta caggttttgg agcattttgg    27840
atttcagatt tttggattaa cctgcattaa tgctcaacct atatgaaatt ttattccttt    27900
ttatggctga ataatgttcc actgtatgta tatactacat tttgtttatc cattcatctg    27960
ttaacagaca cttaagttat ttccacattt tgggtattat aaatagtgct gctgcgaaca    28020
ttggtgtaca tgtatctgtt tgagtccctg tttttagtta ttttggttat atacctagga    28080
atggaattgc tgatcatatg gtaattctgt gtttaacttt ttgaggaact accactgttt    28140
tccacaatgg catcaccatt ttacattccc accagcaatg cacaaagatt tcagtgtctg    28200
tatccttgct aacacttatt ttccattttt tgagttttt tgttttgttt ttttaataat    28260
agccaatcct aatgggtatg tggtagcatc tcatggtttt gatttatttt tcctgactat    28320
tgatgatgtt gagcatcttt tcaggtgctt agtggccatt tgtccgtcat ctttggagca    28380
ggaacaatgt cttttcaagt cctttgccca ttttttaaatt gaattttttg ttgttgagtt    28440
gtatataaca cctttttga agtaaaaggt gcactgtaat aatccagact gtgtttctcc    28500
cttctcagga ttcctacagg aagcaagtag taattgatgg agaaacctgt ctcttggata    28560
ttctcgacac agcaggtcaa gaggagtaca gtgcaatgag ggaccagtac atgaggactg    28620
gggagggctt tctttgtgta tttgccataa ataatactaa atcatttgaa gatattcacc    28680
attataggtg ggtttaaatt gaatataata agctgacatt aaggagtaat tatagttttt    28740 atttttgag tctttgctaa tgccatgcat ataatattta ataaaaattt ttaaataatg    28800
tttatgaggt aggtaatatc cctgttttat aaatgaagtt cttgggggat tagagcagtg    28860
gagtaacttg ctccagactg catcggtagt ggtggtgctg ggattgaaac ctaggcctgt    28920
ttgactccac agccttctgt actcttgact attctacaaa agcaagactt taaacttttt    28980
agatacatca ttaaaaaaga aaccataaa aagaatatg aaaagatgat ttgagatggt    29040
gtcactttaa cagtcttaaa agcaatcgtg tgtatagcat agaattgctt ggattggata    29100
aacagtggca ttatatattt taaaaaataa aagttttgaa agattgaaga atttgggcat    29160
tacagttctc ttaaatctga caaagctgca taaaactatt aaaataatca ttattatact    29220 atttatatt ctatttcttt gagggtttag ttttccaaaa actacatatt aagcaaatga    29280
atcactcagt ggctatgtca tataataacg agttagccta gttataagaa gtttaacatt    29340
ttatttaaga acattgttac agcatgtta ctgtatagtc tagtaataga ggaaaagaca    29400
tttgggtggg tggtagtggt agtattttta tagaggagtt accaaatttc agctctatta    29460
tccaagttta cccagctaat ggtgttcgga accgggaatt tgagccaatt ctgactctgt    29520
tgtctgctct gctccttctt ttgtgctgtg tctttgaaag tcacctaaaa ttgtgaggga    29580
atgtaatttc accccaaatt tagagtttat gcacttgtta tattgaaaat gattaacatg    29640
tagaagggct tttaatggaa taagtggtgt agtaacttca gtgttgccta cctagaaatc    29700
```

```
aaaatctttc tagttgtcca ctttgttttt tgaaaaagta atatgaaaat tatgttaatg    29760
ctttaattca ggttttttgta aaatatttt tatctttaca catttaacat acgtttctaa    29820
aattatagtc tgttatatag cactttgggt ctagaatttt tcagtagttt ctgttttact    29880
attatgatct acctgcatat taacctatta ggttatagtt ttactatact tctaggtatt    29940
tgatcttttg agagagatac aaggtttctg tttaaaaagg taaagaaaca aaataactag    30000
tagaagaagg aaggaaaatt tggtgtagtg gaaactagga attacattgt tttcttcag    30060 ccaaattta tgacaaaagt tgtggacagg ttttgaaaga tatttgtgtt actaatgact    30120
gtgctataac ttttttttct ttcccagaga acaaattaaa agagttaagg actctgaaga    30180
tgtacctatg gtcctagtag gaaataaatg tgatttgcct tctagaacag tagacacaaa    30240
acaggctcag gacttagcaa gaagttatgg aattcctttt attgaaacat cagcaaagac    30300
aagacaggta agtaacactg aaataaatac agatctgttt tctgcaaaat cataactgtt    30360
atgtcattta atatatcagt ttttctctca attatgctat actaggaaat aaaacaaatat    30420 ttagtaaatg ttttgtctc ttgagagggc attgcttctt aatccagtgt ccatggtact    30480
gcttttggct ttggtttctt tctacattga aaatttctct tcaattctga gcacatgtta    30540
acatttagaa ttcaagaggt ggggattttt ttttcccatg gttacatata tatatatata    30600
tatatatata tatatatata tatatatata taaaagaac agggcaacaa attttgcgt    30660 tttctatttc ggtagtactt ttaaaccatt atgtcatgtt tctaggttaa acgttgttgt    30720
atttgaagaa ttttactttg gcagaatttt tttgaggatg tgtttatttc tggagaaagg    30780
tctcattaaa gaaagacaat acccagaaag ccaacagaaa ttctgttact catttaatgc    30840 attttctga caaaaattat tgccagagag aacctgaatt ttgtttcaaa aatcatcttt    30900
gttttaaaaa tgacttttc ttcaggtaaa ataaataat ttcagttgct attatttaac    30960
ctgtttgtat gaagagttta acatatagga aatgaataca taaagatagg aaggaattaa    31020
ttgttatatg tagtcatatg tctcttaatg acagggatac tttctaagaa atacattgtt    31080
aggtgatttt gtcattgtgc aaacatcata gaatatactt acacaaacct tggtagtata    31140
acctactata cacctgggat atgtagtata gtctcttgcc ccagggatac aaacctgtac    31200
agtatgtaac tgtactaatg actataaggc aattgttaac acaatggtaa gttttgtgtg    31260
tctaaaccta cacttgggct accctaagtt tatatatttt tttaaatttc tgttcaataa    31320
taaattaacc ttactttact gtaacttttt aaactttta atttttccta acattttgac    31380
ttttgtaata cagcttaaaa cacacattat acagctatac aaatttttct ttccttatat    31440
ctttattctg taagcttttt tccatattta aaattttttg tttgttttta cttattaaac    31500
ttttttgtta aaaactaaga catgcatgca cattaaccta ggcctacaca gggtcaggac    31560
catcaatatc attgtcttcc acttccacat cttgtcccac tggaagatct tcagggcag    31620 taacacacgt ggagctgtca tctcctataa taacattgcc ttcttttgga atacctcctg    31680
aaggacctat ccaaggctgt ttatagttaa cttttttttt tttttttttt tttttttagt    31740
aaataggagg agtacactat aaaataacaa tataggtgct ataccattat acaactgaca    31800
gtgcagtagg tttgtttaca ccagcatcac cacaaacacg tgagcaatgt gtcgtactac    31860
agtgttagga tggctataac atcactaagc aataggaact tttaaactcc attataatct    31920
tatgggacca ctatcacata tgcaatctcc tgtggaccaa aatgtcatta tgtggtacat    31980
gactgtacta agaaattgat ccatctatat tccatcaatt tgtttagggc ttttttctggt    32040 tacatttacc tgtgagccca gaaaaccagt tttgtagaaa ttaacttctg taatgctagg    32100
```

```
agttaaaaaa aattgctgaa caacttttac attgttaaac atttaaaaac aagcgttcta    32160
gaagtttatc aaatttcata aaggtgcaaa aatgtaaatg taaatcatta tccagctaat    32220
atatatgttg tatttcccta gtaggagagc atatgtacct cttcctagtt atacaaattt    32280
gatatatagt aaagaaacag taaattctac ttcaagtcat tttgggagga ttaaaaactg    32340
aatttctcta gtttgaccat tgtacagatt tatctggcaa ttttactaaa acctgattta    32400
taggttaaac ttggtgtata tcatatatca ctttacttta gaggaattaa gatttcacat    32460
aaatccattt ccaggttcca aagaccagga agaggcttgg ttttgtttt tcttttact    32520 gtctttacag tctccttgac tttcttagg agagaaggta ctgagaaaac atgattctaa    32580
tatttattat ttttcttcc aacatttct tatgaaacat tttcaaatac aaaattgagt    32640
tttatttaaa acatttgcaa atatactacc tagattctac cattgttgtt ttatatttgc    32700
tttacttaca actttaaaa gatgcttttt ataccactga acattttagc ttacatttca    32760
caaagaaaag aaaaaattta agagactttg cataatgttt taaggggttg cagtaaagaa    32820
gtgcttctta tattttctta tgcatacaaa tcagctgggc ttattaaaat ccagattcta    32880
attcagaagg tttaggtggg gaccgagtct gcatttctaa caaactccta ggtggtattt    32940
ttcttggtac ttggaccata ctttgagtag aaaagcagta gaggacataa aaagagtctt    33000
gttagtccca ctttgttgct gtccacttct catttgataa tatcctaaaa tagctgtgtc    33060
tcctttttgg tggttgtatg attactacct cagaagtact aattgattct tgctatttga    33120
ccttaatact ttaatataac acagcattca tatttgatca gaaaactatc tggcttcctt    33180
ttataagaga ttttttaggtt ttatacagtt ttgtggcctt gggtttttt gtttgatttg    33240 tttttttgaa ggtatataat atgtaagtag ataaacaaat ttgatttgta gacatttta    33300 tgtggatcat ctaattaaaa atggagggat acagtatgaa agaatacttg tacttcttaa    33360
cagagcactc aaccttttctt ttacatcctg tttcactgat gttattatgt aatttatgtt    33420
gctaaactat aaattagata tttaatttct gttctttgat ttccttttat tattaaatgg    33480
acttgttgat ttgcctagaa attaatttgc ctttcaaaag tcttattaat cttcctccgt    33540
tgaaattaat ttgatatttg catgcttctg gaagacttta aagagctatt ccgagtaact    33600
gtagagatta taaatgaaa tatgggaatt ttaataaatt ttacatctcc agttactggt    33660
gaaaatgtca agtcctcctt tctgcagagt attttgttac tcatctgtta ttcagcttat    33720
ttatttattt atttatttat ttatttttct ttctttcttg ttttttttt ttgagacgga    33780 gtcttgcttt gtcgcccagg ctggagtaca gtggtgggat cttggctcac tgcaggctcc    33840
gcctcccggg ttcacaccat tcttctgcct cagcctccca gtagctggga actacaggca    33900
cccgccacca tgccttgcta aattttgta tttttagtag agacgggttt cactgtgtta    33960
gccaggatgg tctcgatctc ttgacctcgt gatccacctg cctcggcctc ccaaagtgct    34020
gggattacag gcatgagcca ccgcgcctgg cccttatttg ttttttaaac aaaattagtg    34080
tgcatatcct tgttgtattt tatcggcaag ttgttttatg ccctaacttt tggggtcttg    34140
atcatgagcc taaacacgt aaacacccaa aaagaattat attccggtta aaggaacaaa    34200
acattcattt agaagttctc atccatgtaa atcagaggct ggcaaatatt ttctgtaaag    34260
ggccaagata gtaaatgttt taggctttga gggccacaag tggtatctgt tgcatttttt    34320
tttaattatg acccttttaaa atgcaaaaat cgttgttagc ttgtgcatag tataaaaata    34380
ggctggccgc atgctgtggc tcatgcctgt aatcccagaa atgaggtggg aagccgaggt    34440
```

```
gggcacacca cctgaggtca ggagttcgag gccagcctgg ccaacgtggt tgaaacccc      34500 tctctactaa aaatacaaaa cttagccagg cgtggtggcg ggtgcctgtt atcctggcta     34560 ctcaagggc  tgaggcagta gaattgcttg aacctgagag gcagaggctg tagtgagccc     34620
agatcaagcc agtgcacacc agcctggacg accgagcgag actctgtctc aaaaaaaaaa     34680
aaaaaaggct gtggctgcat ttggtccatt ggctgtaata tgctgattcc taattctctg     34740
ggtaacttta gtgtttgatt agctactaga agtaggttaa acttttgta  ttttacaggc     34800 taactttaat aatcttaaag taaaacttaa catagttcat ggaaaggaaa tagaaatttt     34860
accctagtac tcttttttt  ttttttttt  tttttgagg  cagagtctcc ctctgtcacc     34920
caggctggag tgcagtggtg ggatcttggc tgattgcaac ctcctcctcc tgggttcaag     34980
caattcttgt gcctcagcct cccgagcagc tgggactaca ggcacgcacc accacacctg     35040
actgattttt gtattttag  tagagacagg gtttcgccat gttggccagg ctggtcttga     35100
actcctggca tcaagtgatc ctcccatctg agcctcccag tgtgctggga ttacagacgt     35160
gagtcactgt gcctggtctc tagtatttt  ttttttttg  agacggtctc actgttgcca     35220
ggctggagtg cagtggcgcg atcctggctc actgcaacct ccgcttccg  gattcaagcg     35280 attttcctgc ctcagcctcc tgagtagctg ggactatggg tgcacaccac cacgcccagc     35340
taatttttgt attttagta  gagacggggt ttcaccatgt tggccaatat ggtctcaatc     35400
tcttgacctc gtgatctgcc cgtctcggcc tcccaaagtg ctgggattac aggcgtgagc     35460
cactgtgccc agctgtactt tttaagataa gaattgcagg gtatatattt ttaccaactt     35520 ataacttat  aattttaaaa agctaattac ttggctagaa tataatgcgt tacatattct     35580
ttacactcag ttcagtccat atctgaaagg caaatagaat tattttctgc tagtacattg     35640
tgtagtccct atgttcctag tgtataagga ctgttaccta gttcacattt atctgggttt     35700
ttgacagatt ttcctggtcc ctttggacag tgcatggcca tgttggcaaa agctgtcaaa     35760
attgaaacat tgacaccatg agaattgtgt gttttccagt ctgctaaaat caaaagtggg     35820
agggttcagt aaggtgaata acagaagcag agtttttcggg gtatctgtta ctcctcattc     35880
ggcttttctg ctctctgggg gtctcaattt aaatataatg tgaaaattag ttttacgaac     35940
ctaaaaatgt tgagtgattc atttcctggt tttgttgtta atttctagat attttaaatta    36000 attgttagaa gaaccccgtt aaagaatgct ttgcaaaaca acctccttat gtgctatgtc     36060
tctgtttaat agtagttgag tttgtgtaca tgagatcaat attttgaact atagcttttt     36120
atgagttaaa aattgacgga acagttactg tgcacttgct gtgcaccatg gtagtctccc     36180
aagtagtggt tttctgcat  ttcaatagta catgagatag gctgtgggtg gcaaggtttc     36240
ttgagaaagt gagggatgca cagttgggtt ttagaataca tcttgttcct ccatgccctt     36300
ccccaccaaa aggctggtag tcttgcattt gtatatagtt agggtatttg atgtgttgct     36360
tccttgacag agttttgcaa gaatttgcag atttaacagg aacaaaaact tacttaaaac     36420
aaaatctctt agtaaaagca tagtctagca agatttagaa tgatactttg gctaacagta     36480
ctttctctat atggagtgct ttgttccat  agcctcacaa gtatgttttc agataatagt     36540
tgagttgaaa atgttgtcaa tctccttgatt ttaaaaaatt tacatatttta aagttgtata    36600 cttttgttcc tacgtatttt cagttgttct taaagtttaa taagtgacat ttgaaaatga    36660
gtatatgtgt ataaaaacaa agtaggcta  ggcacggtgg ctcatgccta taatcctagc     36720
actttgggag gctgaggcag gcggatcaca aggtcaggag tttgagacca gcctgggcaa     36780
tatggtgaaa ccccccctcta ctaaaaatac aaaaattagc tgggtgtggt ggtgcatgcc    36840
```

```
tgtagtccca gctactcagg aggctgaggc aggagaatcg cttgaacccg gaggtggcgg    36900
ttgcagtgag ccgagattgc accactgcag tccagcctgg gcggcagagc gagactccat    36960
ctcaaaaaaa aaaaacaaaa aaagaaaaag ttaaaaaaaa acaaaaaacc cccacaaaat    37020
gagtatatgt ggcaacaagt cctattctca aaaaaattat tgtgtgctag ttaagagctt    37080
aatgagtagc cagtcggtat taaatatctg tttcagctat attttatctt taaaaattat    37140
ctacagattt tggaatgtga aaaactagtg ttttgtttca taggtatata ctgtaggcat    37200
tttaaaaata agagccagtg ccagtggttt acagtgtaca caaggataat gttctcatgt    37260
tctcttgatg tcagtatgac tttaaagcat attatcaaga ataactaag tctgaaaaac     37320 tgtggtaaat aactggtact ctaaaaccta agtttcttat tactaaaaat aagaaatggt    37380
aaaagtcacc ctgtgctgtt aattatatga gccactgagg tcctgacact gaattcttgg    37440
tggtggataa taatctcttc tttttaatta ttggcttcca attctctctg cattgctgga    37500
aacaaaaatc atatatttca ctattggtgg tggggatgct gtcactgaaa agtagacac     37560 attcatattg attttagaaa taagttaaaa tcaaatttg cttctgctaa attagtagag     37620
gaccaatact gttttctcc ttcatagtat gttttggtac ttctacattg acattataac     37680 ttttttttt ttaaacagaa atagaagttt acattcttag aaaatttatg aaaatatgag     37740
cttttacctg gtttgtgtgt gtgcgtatat atatacacat attttaaat ttcttacatt     37800 gattttcaaa ttgaaagaga accatttgtg aaagtatctt aacagagctc atgctttaca    37860
ttttacatgc tacaaagtta ttttagtgcc ttaaattatt tatgttgctt attaatgaaa    37920
attttggata cataattttt tcaagacaaa ggtaaaaata ataaaccctt tccttctgag    37980
gattaatgat aaatataaac tttaaaacga ttaaaaaaat tttttagag acagggtctt     38040 gctctgttgc ccagactgaa gtgcagtggt gcagtcatag ctcaatgaag cctcaaactc    38100
ctgggcccag gcaaccctcc tgcctcagcc ttttgagtag ctgggacttc aggctcatgc    38160
caacatgcct aatttatctt attttttagta gagatgaggt ctcaaactcc tggcatctct    38220
tgccctctca aagtgctggt actacaggca ttagtcacca cacctgacac ttaaaatctt    38280
ttatatacag gtgtaagtgg gtatctaact taaagtgcca acgaatgtag ttgaaagttt    38340
gtagttggct tagctaacta gttaactaaa ttgattccat taaaaataag ataagactgc    38400
tcttagaata taatgatttt tgttattcgt taaatataaa tatatcactg gatagtatat    38460
gttaatgact tgagatacgc attttaacat ataatcacgt tacttaaatg cctgcctttg    38520
aactgaaact taacattatg aatttaaatt aaagtttgac tttagaggta aatttctgta    38580
ctttactaaa gcagttctta atataattct gagatttcta aaaattagtg tgccctaaag    38640
aattgaggtg tgttttcttt aactactgta ggcagtagat gtacagatga cttctgcatg    38700
caaaaattaa gccctagcca ttggtttact tcaactaata cttagttgcc aattctctgt    38760
gtgtgattga atttaaaact gcaaatggta ctggtgatac attactttt taggtgctag    38820 gtccactttg ttacatttgg ttcagtagaa acattgatgt taccaatctc agaaagctaa    38880
aatatgtatg ccaatcccca aattaggtaa tttattctta attttaagat aaagaaatag    38940
aattccctta aaattaaatg tggagtaaaa tataccagct ttaaaaaata ttcaccttc     39000 tgttagaaga atgaacataa tattacatct tttaatttgc actatatata gattaatatt    39060
tctgtgtatt tctctgtgcc cctactttga tggtatgctt ttctgaacaa actagcagca    39120
cagttaacta agcactttgc cccgtttgat gactgcctaa ttttctagat tggaaaatat    39180
```

-continued

```
taaaaacttt tatctccata tggccaatat atgattgtac ctgttgtcat agctctctta    39240
tgtttaagca agaaaaaccc tattaagagt atttaaatta gaatggaagg cacacagcca    39300
gtatgattga acactgttct aaaaattatt tttaagactt gtagtaaggc caggtttggt    39360
ggctcatggc tgtaatccca gcccttagga ggccaaggtg ggcggatcac ttgtgctcag    39420
gagtttgaga ccagcccggg caacatggca aaaccctgtc tctacgaaaa atacaaaaat    39480
cagtcaggtg tggtggtgct tgcctgtagt cccagctatt tgagaggctg aggcagggggg    39540
atcacctagc ctgggaggtc gaggctgcag tcatgatcgt gccattgcac tccatcctgg    39600
gcaacccagt gagaccctgt ctctaaaaca aaaaataaaa aaagaacttt gtagtaagga    39660
tacaaaatgc tcctattttg tgtgtgtcct ttaattcatg atgtttttat attatggtaa    39720
gcagctctca tttaagattt taataatgta attaaacatg tacagaagac ccagtctcag    39780
cttcacttgt ataccctgga aatagactga aaggtgttaa aatttaagat aaaactcaag    39840
gttccagttt cttgactcac cttttgagatt ctttttatgtt tttgttgttt tttaacaaag    39900
gtttcacgtc catattttac cattttttctt ctcattctcc cctggaggag ggtgtgggaa    39960
tcgatagtat ataaatcact ttttttcctaa gtcaaagaag taattttaaag ctaacttcag    40020
tttaggcttt aattccagga ctagcaaact aaaatggttg cattaattga caaacagatg    40080
ctaatacctg tgtttaggct tgtcataatc tctcctaatt cctaatttaa aaattttaaa    40140
atttaattcc attagaaaac aaaactgact tttaagaaca aaccaggatt ctagcccata    40200
ttttaaaact gcatcctcag ttttattcaa acagtctgat gtctgtttaa aaaaaaaaaa    40260
atctcaagct cataatctca aacttcttgc acatggcttt cccagtaaat tactcttacc    40320
aatgcaacag actttaaaga agttgtgttt tacaatgcag agagtggagg atgcttttta    40380
tacattggtg agggagatcc gacaatacag attgaaaaaa atcagcaaag aagaaaagac    40440
tcctggctgt gtgaaaatta aaaaatgcat tataatgtaa tctggtaagt ttaagttcag    40500
cacattaatt ttggcagaaa gcagatgtct tttaaaggta acaaggtggc aaccacttta    40560
gaactactta ggtgtagtat tctaacttga agtattaaaa gataagaaac ttgtttccat    40620
aattagtaca tttatttta atctagtggg aattaattat aattgagaca attttgatgg    40680
ctgtagtaga ctaatctata tttggcataa agtctaatga tttaatgagt cttaagtaaa    40740
ctaaatattt ggaaactgat atttacctttt attttttaagg gaaagttttt gagataatca    40800
gcagcttttt tttttttttt ttttttttta gtagggagaa aaagatatga gctatagtag    40860
acagcagtaa tattgaatgg cccagaaggt gggaaaaagc cactcttaaa tgtatttttt    40920
cttttggata ttttacaagc aaataataac ttctgcctaa gttcgccatc tcagtggcat    40980
cagcagcaca gcactttctt atcccagtga gaaacctggg aatttttagga tgactcctac    41040
cgccctcttt tcccctggt ttggaagtat ccacaaattc ctgtgacgtt acattctgtg    41100
tcttttatgt catcattagt tcaggcccct atcatttctt gttggactgt tagaacctcc    41160
tatttggttt accagttgct gccatcattc attgtgaaac cggagagata cactttaaag    41220
aaatgtcatt tttggccggg cgcggtggct cacgcctgta atcccagcac tttgggaggc    41280
ctaggcgggg gatcacctga ggtcaggagt tcaagaccag cctggctaac atggtgaaac    41340
cctatttcta ctaaaaatac aaaaaattag ccgggcgtgg tggcacgtgc ctgtaatccc    41400
agctacttgg gaggctgagg caggagaatt gcttgaacct gggaggcaga ggttgcagtg    41460
agctgagaat gcaccattgc actccagctt gagcaacaag agcgaaactc tgtctcaaaa    41520
aaaaaaaaaa aaagtcattt tagctataga ataaaatctc atgttccaca tgtgttgcag    41580
```

```
atagtcctta ctaccttccc accactccag ctctttttg gtcttatatc taaaaacgtc   41640
atcttgcctg aatttctttt gttcttctat aaataaatac catgttattt cctaccttcc   41700
cttgagtctt ggctcttgtt tggaatgcca gtatttttat ccctagtctt actaattagc   41760
taacactctc atgattcccc agtctcctac tctctaaaaa cctttcttta aacccttaga   41820
ctaggcatgg agcccttcct gtgtattccc agaatactat tcttaactat tatatgcttc   41880
ccatgttatg ttgaaataac taacctcttc tgtttcattc ctatattact tgacagcaaa   41940
atcttagcca gaattacata ttttttaatct ttgcacaccc attgcctagt aaggttcctg   42000
ggacatagta actacccagt aaatatttat tgcgtggaat tctcatttc gtttctaaac   42060 ccgtattaaa ctctgtcttg ctcagaaaat acttcactag gtatcataaa gttcatggca   42120
gagcttaagc tttggatgca tattgtttgt aatatatcat gttcttaaga ataggcaata   42180
aaattacagt tttcaaaaac tactacattt attatattta ttacaagttg gtgttcttta   42240
ttacatgaat tttaggtatt tcccaaaagt ataaaatata catttgaata gtagactcaa   42300
tcccaaaaga tactacgtgg tgtactaatc tactaaactc agaaacaaag catgactggc   42360
attaattttt gttgaaattt atgaactctg aatgttttg aatatcattc tgtaaagcaa   42420
tattttgcaa ttaaagcaat tttgcatgtt aaatttacc acaacctcta aaatattgca   42480
aatttaacaa tacagtttga aaagttacac atttttaaata acagtaccat gaccagattt   42540
aggtggtggt tttaattttt tattttctcc tcctattgtc tcaccattag atgattttaa   42600
aaatagaatt gttagagta aaataagtgt tatgctctaa tttatattta aaatgaaggt   42660
ttaagcacgt actattctaa aatttctaat ttgtgcaaat tatgttttat acagtgactg   42720
taggtgaatg tcacaattgt ttgatgtgac gaatccttgt ttttcagtac acgtggaagt   42780
aattcatata aagagaagt atacttggta attaaaaatt taaaattaaa tacaatttaa   42840 aaaaaattt attttgacaag ctggctgtgg tgtgtgtgcc tgtagtatca gctgcttggg   42900
agcctgaggc aggaggattg cctgacccca ggagtttgag gttgaaggga gctatgatgg   42960
tgccatggca ctgtagccta ggcaacagaa agagactcca tctcttaaaa aaagtaaaaa   43020
taaaaaaatt ttggcacagg gacagtggct cacacttata atgccagaac tttaggagtc   43080
cacagcgcga ggactgcttg aggccaggag tttaagacca gactgggcaa cgtaatgaga   43140 ccccacctttt aggaaataaa tacataaata aaaatttgac aatgataaac atatataaat   43200
tagcttttct tagtcctgaa aaagataatg ttatgtgtat gtgtgagaat gattagttct   43260
catatgagaa aaaagaatt cattgctctg tgtaggttgt gacatttcct tcacgattga   43320
aattaattaa ttttttttta ttacttattt atttttaaaa tagagacagg ttcttgctgt   43380 gttgccagg ctggtctcaa actcctggcc tcaagcagtt ctcctgcctc agcctcccaa   43440
attgctgtga ctgtaggtgt gagccactgc actgggccaa aattacttaa ttttaacaag   43500
atgatgtaga gaggagagtt cattgcaaca taagcctaga atctttgtca gaatcttagg   43560
aagtaatgtt ttcaaattct gtgttttcac cataaaatgt gtcttctctg tgtccatcac   43620 atggttttc attgttttct gctttaccat tttagtacca ttggcatttt tcttcattgt   43680
aaaagtagta gaaatggagt agattacata aggatgtgat cagagggaat ttattcattc   43740
agggtaaggg agttagatcc tcttttaaga ttctatcaca ttctaagggt ttatgattct   43800
aaactgtcaa gtaaattgtc aagtgctggc aagctacaga ataatttta ttgtatcatt   43860 ggaaattttc ccctctatat gtgttaaaga gtttagcctg aagggataca tacacataca   43920
```

```
tatatgtaat caaaccttga tggtattgta ttgctgataa attatttctt accacttttc    43980
ctttctcctg tgggagaaac aaaagcatat gtttgtgtag tatcagtaat gatattagag    44040
agtgggaaac atcagtgagt gcagtttggg gactttattg gagactttca ctagtgctca    44100
aataaataat gctggttttt atcctactgt ttgcttaatg tggactagcc tcttattccc    44160
attctatgtt tacctctctt aaaatattgg tcacgctttc ttgaattata gatctattag    44220
gaaaattcat gaactgtagc taattttcat tgttcatgct ccagatttat tttgaaatat    44280
cgttaatctt agtagtacag taaaggagaa ataccactta acattttttg ttttttttc    44340
tttgagacag agtcatgctc tgtcacccag tctggagtgc agtggtgcta tctcggctca    44400
ctgcaatgca cttcgcctct ccgggttcag caattctcct gcctcagcct cctgagtagc    44460
tgggattaca ggcacctgct accacaccca gctaattttt gtatttttag tagagacagg    44520
gtttcaccat gttggccagg ctggtctgaa actcctcacc tcaagtgatc cacccgtctt    44580
ggcctcccaa agtgctggga ttacaggctt gagccaccgc accccgccca cttaacattt    44640
taaattaatt tcaagataat atcacttgaa atttttaca catataattt ttttaataca    44700
tttatttaca cagtttataa tatcctacaa agtgattaca atgagtaaaa acccagtttt    44760
cattgttcct aaagtggctt gatttataca acttaatgtg ttgggtattt gtttctaaga    44820
ctccctctgc tgtctaggtt tggaagtatt gtgaggttaa cagattttct ttttatagtt    44880
actactcagt tgaacaggct ttaaaataca gagagaatca tatttttttct tcattttttg    44940
cttttattta tattttttctt ttaattggag acatgacaag aattgacttg tgtatggatc    45000
ttgcataatt taagtactgc aggttttaaaa tctactacca gtttgagagt gccatttttc    45060
acactgtaga ttattaggtt gaaaagtatt atggcttaaa atcgctttta gccattaaat    45120
ttaataacc ttgctttaat cataaataga tggtggtcac aatgactaac tgttaaactc    45180
tttgaagaca ggatatttgg ctttatatgg caagcttttg aatacaacag aaattaaaac    45240
tttatgggat agaaagaatc tcctccaaat tggtaaacta taagaccttt caaatgattt    45300
agctaatttc tccacaaatc tgaggtatta gtgttttttt taaagtggta ttctcctgtg    45360
ttggggtcac tttaaacctt tttcttaatg ataaatatat gaattgaaac taatcccta    45420
atatatatca tttgaaaact gaaataatat gtttagatac tgtttacttg ttgataaatt    45480
attggaatag gatgttcgaa tactgtttac ttccttggtaa attttaaat ccaatggatt    45540
ttacgtaagt atagaactgg agctcaaata ctgttactgt gtgtgaagat atatgaacat    45600
agtttacagt tgcatggctt atatctaaag tccagaaaca taaggacaat taagtgtaca    45660
cacacacaca tgcatttgga ttttgatgac ttaggtttgc caatgtggaa aaaatagtag    45720
caaattaagt tctcctgtga aaagtcgtt accttattta aaattctgtg ccattggtta    45780
tccttgtctt ttgtgaaaat tagtgttcct gtttataata ttgacaaaac acctatgcgg    45840
atgcacttta agaattctaa aagtcctaat atatgtaata tatattcagt tgcctgaaga    45900
gaaacataaa gaatccttc ttaatatttt ttccattaat gaaatttgtt acctgtacac    45960
atgaagccat cgtatatatt cacatttta tactttttat gtatttcagg gtgttgatga    46020
tgccttctat acattagttc gagaaaattcg aaaacataaa gaaaagatga gcaaagatgg    46080
taaaaagaag aaaaagaagt caaagacaaa gtgtgtaatt atgtaaatac aatttgtact    46140
tttttcttaa ggcatactag tacaagtggt aattttttgta cattacacta aattattagc    46200
atttgttta gcattaccta atttttttcc tgctccatgc agactgttag cttttacctt    46260
aaatgcttat tttaaaatga cagtggaagt ttttttttcc tctaagtgcc agtattccca    46320
```

```
gagttttggt ttttgaacta gcaatgcctg tgaaaaagaa actgaatacc taagatttct    46380
gtcttggggt ttttggtgca tgcagttgat tacttcttat ttttcttacc aattgtgaat    46440
gttggtgtga aacaaattaa tgaagctttt gaatcatccc tattctgtgt tttatctagt    46500
cacataaatg gattaattac taatttcagt tgagaccttc taattggttt ttactgaaac    46560
attgagggaa cacaaattta tgggcttcct gatgatgatt cttctaggca tcatgtccta    46620
tagtttgtca tccctgatga atgtaaagtt acactgttca caaaggtttt gtctcctttc    46680
cactgctatt agtcatggtc actctcccca aaatattata tttttctat aaaaagaaaa     46740 aaatggaaaa aaattacaag gcaatggaaa ctattataag gccatttcct tttcacatta    46800
gataaattac tataaagact cctaatagct tttcctgtta aggcagaccc agtatgaaat    46860
ggggattatt atagcaacca ttttgggget atatttacat gctactaaat ttttataata    46920
attgaaaaga ttttaacaag tataaaaaat tctcatagga attaaatgta gtctccctgt    46980
gtcagactgc tctttcatag tataacttta aatcttttct tcaacttgag tctttgaaga    47040
tagttttaat tctgcttgtg acattaaaag attatttggg ccagttatag cttattaggt    47100
gttgaagaga ccaaggttgc aaggccaggc cctgtgtgaa cctttgagct ttcatagaga    47160
gtttcacagc atggactgtg tccccacggt catccagtgt tgtcatgcat tggttagtca    47220
aaatggggag ggactagggc agtttggata gctcaacaag atacaatctc actctgtggt    47280
ggtcctgctg acaaatcaag agcattgctt ttgtttctta agaaaacaaa ctctttttta    47340
aaaattactt ttaaatatta actcaaaagt tgagattttg gggtggtggt gtgccaagac    47400
attaattttt tttttaaaca atgaagtgaa aaagttttac aatctctagg tttggctagt    47460
tctcttaaca ctggttaaat taacattgca taaacacttt tcaagtctga tccatattta    47520
ataatgcttt aaaataaaaa taaaaacaat ccttttgata aatttaaaat gttacttatt    47580
ttaaaataaa tgaagtgaga tggcatggtg aggtgaaagt atcactggac taggaagaag    47640
gtgacttagg ttctagatag gtgtctttta ggactctgat tttgaggaca tcacttacta    47700
tccatttctt catgttaaaa gaagtcatct caaactctta gttttttttt tttacaacta    47760
tgtaatttat attccattta cataaggata cacttatttg tcaagctcag cacaatctgt    47820
aaatttttaa cctatgttac accatcttca gtgccagtct tgggcaaaat tgtgcaagag    47880
gtgaagttta tatttgaata tccattctcg ttttaggact cttcttccat attagtgtca    47940
tcttgcctcc ctaccttcca catgccccat gacttgatgc agttttaata cttgtaattc    48000
ccctaaccat aagatttact gctgctgtgg atatctccat gaagttttcc cactgagtca    48060
catcagaaat gccctacatc ttatttcctc agggctcaag agaatctgac agataccata    48120
aagggatttg acctaatcac taattttcag gtggtggctg atgctttgaa catctctttg    48180
ctgcccaatc cattagcgac agtaggattt tcaaacctg gtatgaatag acagaaccct     48240
atccagtgga aggagaattt aataaagata gtgctgaaag aattccttag gtaatctata    48300
actaggacta ctcctggtaa cagtaataca ttccattgtt ttagtaacca gaaatcttca    48360
tgcaatgaaa aatactttaa ttcatgaagc ttacttttt tttttggtgt cagagtctcg     48420
ctcttgtcac ccaggctgga atgcagtggc gccatctcag ctcactgcaa cctccatctc    48480
ccaggttcaa gcgattctcg tgcctcggcc tcctgagtag ctgggattac aggcgtgtgc    48540
cactacactc aactaatttt tgtatttta ggagagacgg ggtttcaccc tgttggccag     48600
gctggtctcg aactcctgac ctcaagtgat tcacccacct tggcctcata aacctgtttt    48660
```

```
gcagaactca tttattcagc aaatatttat tgagtgccta ccagatgcca gtcaccgcac   48720
aaggcactgg gtatatggta tccccaaaca agagacataa tcccggtcct taggtagtgc   48780
tagtgtggtc tgtaatatct tactaaggcc tttggtatac gacccagaga taacacgatg   48840
cgtattttag ttttgcaaag aaggggtttg gtctctgtgc cagctctata attgttttgc   48900
tacgattcca ctgaaactct tcgatcaagc tactttatgt aaatcacttc attgttttaa   48960
aggaataaac ttgattatat tgttttttta tttggcataa ctgtgattct tttaggacaa   49020
ttactgtaca cattaaggtg tatgtcagat attcatattg acccaaatgt gtaatattcc   49080
agttttctct gcataagtaa ttaaaatata cttaaaaatt aatagtttta tctgggtaca   49140
aataaacagg tgcctgaact agttcacaga caaggaaact tctatgtaaa aatcactatg   49200
atttctgaat tgctatgtga aactacagat ctttggaaca ctgtttaggt agggtgttaa   49260
gacttacaca gtacctcgtt tctacacaga gaaagaaatg gccatacttc aggaactgca   49320
gtgcttatga ggggatattt aggcctcttg aattttttgat gtagatgggc attttttttaa   49380 ggtagtggtt aattaccttt atgtgaactt tgaatggttt aacaaaagat tgttttttgt   49440
agagatttta aaggggggaga attctagaaa taaatgttac ctaattatta cagccttaaa   49500
gacaaaaatc cttgttgaag ttttttttaaa aaaagctaaa ttacatagac ttaggcatta   49560
acatgtttgt ggaagaatat agcagacgta tattgtatca tttgagtgaa tgttcccaag   49620
taggcattct aggctctatt taactgagtc acactgcata ggaatttaga acctaacttt   49680
tataggttat caaaactgtt gtcaccattg cacaattttg tcctaatata tacatagaaa   49740
ctttgtgggg catgttaagt tacagtttgc acaagttcat ctcatttgta ttccattgat   49800 ttttttttttc ttctaaacat ttttcttca aacagtatat aacttttttt aggggatttt   49860
tttttagaca gcaaaaacta tctgaagatt tccatttgtc aaaagtaat gatttcttga   49920 taattgtgta gtaatgtttt ttagaaccca gcagttacct taaagctgaa tttatattta   49980
gtaacttctg tgttaatact ggatagcatg aattctgcat tgagaaactg aatagctgtc   50040
ataaaatgaa actttctttc taaagaaaga tactcacatg agttcttgaa gaatagtcat   50100
aactagatta agatctgtgt tttagttaaa tagtttgaag tgcctgtttg ggataatgat   50160
aggtaattta gatgaattta ggggaaaaaa aagttatctg cagatatgtt gagggcccat   50220
ctctcccccc acaccccccac agagctaact gggttacagt gttttatccg aaagtttcca   50280
attccactgt cttgtgttttt catgttgaaa atacttttgc attttttcctt tgagtgccaa   50340 tttcttacta gtactatttc ttaatgtaac atgtttacct ggaatgtatt ttaactattt   50400
ttgtatagtg taaactgaaa catgcacatt ttgtacattg tgctttctttt tgtgggacat   50460 atgcagtgtg atccagttgt tttccatcat ttggttgcgc tgacctagga atgttggtca   50520
tatcaaacat taaaaatgac cactctttta attgaaatta acttttaaat gtttatagga   50580
gtatgtgctg tgaagtgatc taaaatttgt aatattttg tcatgaactg tactactcct   50640
aattattgta atgtaataaa aatagttaca gtgactatga gtgtgtattt attcatgaaa   50700
tttgaactgt ttgccccgaa atggatatgg aatactttat aagccataga cactatagta   50760
taccagtgaa tcttttatgc agcttgttag aagtatcctt tatttctaaa aggtgctgtg   50820
gatattatgt aaaggcgtgt ttgcttaaac ttaaaaccat atttagaagt agatgcaaaa   50880
caaatctgcc tttatgacaa aaaaatagga taacattatt tatttatttc cttttatcaa   50940
agaaggtaat tgatacacaa caggtgactt ggttttaggc ccaaaggtag cagcagcaac   51000
attaataatg gaaataattg aatagttagt tatgtatgtt aatgccagtc accagcaggc   51060
```

-continued

```
tatttcaagg tcagaagtaa tgactccata catattattt atttctataa ctacatttaa    51120
atcattacca ggaactgttt gttttgtagt gaaccttgag tatgtgctgt taatatacca    51180
aattgggtga aaaataagg gattcctttc aaaagttaag agaagtaagt gtgtaagaaa      51240
ttattttgct tattaaatgt tcggtaaatg gcattctctt gtcagtaaaa tggagaaata    51300
agctaaaaat aattggctaa gtcctattaa gttagaggat taagtgtatt atattttcat    51360
tcaaaattgg gtgctcatta atttatgatc ggtagtatag ctaaattgct atgtttgtat    51420
caaaattgag cataaagttg ctgatacttt ctccgtatga acagaagttg aaacctattt    51480
agttcagtag ggcagctcag ggatttttta cacaacatgt atatcttccc attttaagtt    51540
agaattattt tacaacatct ggtatacata aacagctggc actgatagct aaattaaagt    51600
agtaatgatc aattagtttt gttggtatct gaataatagc gttgtttcat agctctgtat    51660
ttcctaagga agtacaaagc ttctagctct ttcattacaa attcgccctg tgcaataagt    51720
tctttgatct tctctggatt cttcacatct ttgtttttaa ggaaaatgtt cttcaaacgc    51780
tttttaaaat agtctgctcc ttttggatag tctcgtccaa gatacagcag cttcaaaaag    51840
aaagattata tatttctaaa caatccatgt catataataa cattttttata aaattggcaa   51900 cataattact tacatttta taaagttttta gtacttctcc tcttaaagaa ttggccattt    51960
tcatttatca tgtaaattat ccacttttat gcataacata cctaaagaaa ggaaaatttt    52020
tttgcaatta gctgcattgt agtcttaaaa aaataaaaaa aggttataca cattgagaaa    52080
atggtaacct ttttacatt caataaatat ttcttgataa cttttcgtt ccacgtactg      52140 ggatatagtt ataaacactt ccgataaaat tacctgctgt cataattgac gttttcctat    52200
gggagacata agcaaagaca attgtgattg tgagaagtca catgaaggaa atgagaaagt    52260
ggattgtcat cacagatagg tacgtgtacc tccttttatg ccacagtgga atgagttaaa   52320
ctagatttaa attccagttg cataatgtac agattaatta accttgctga gcctgagttt    52380
tccttatcaa caaacaagag attatcttta ccctgctctc aaggcaaggc cagagccact    52440
tgaaggacat tgagcagaag cctgatcaaa tgctgatggg tgcttatcca aagggaggct    52500
gaaaactagc agaaactggg tgagttaagc aggttggaat agtagatggg cagtaagatt    52560
ggtggtgaag aggccaaatg aacaacctgt aagagggtgt ccctgaggaa caggcaaaat    52620
catgcttctt tatgtgtaat gtgttaactc tactttgtag aggaggctcc aaact         52675
```

<210> SEQ ID NO 2
<211> LENGTH: 20
<212> TYPE: DNA
<213> ORGANISM: Artificial Sequence
<220> FEATURE:
<223> OTHER INFORMATION: F9(2724)D RD-PCR primer

<400> SEQUENCE: 2
atgtagccac tatgcctatc                                                20

<210> SEQ ID NO 3
<211> LENGTH: 20
<212> TYPE: DNA
<213> ORGANISM: Artificial Sequence
<220> FEATURE:
<223> OTHER INFORMATION: F9(3210)U RD-PCR primer

<400> SEQUENCE: 3
ctggctgtta gactcttcaa                                                20

```
<210> SEQ ID NO 4
<211> LENGTH: 22
<212> TYPE: DNA
<213> ORGANISM: Artificial Sequence
<220> FEATURE:
<223> OTHER INFORMATION: RAS(5445)D RD-PCR primer

<400> SEQUENCE: 4
ctggtggagt atttgatagt gt                                          22

<210> SEQ ID NO 5
<211> LENGTH: 20
<212> TYPE: DNA
<213> ORGANISM: Artificial Sequence
<220> FEATURE:
<223> OTHER INFORMATION: RAS(5857)U RD-PCR primer

<400> SEQUENCE: 5
gaacatcatg gaccctgaca                                             20

<210> SEQ ID NO 6
<211> LENGTH: 20
<212> TYPE: DNA
<213> ORGANISM: Artificial Sequence
<220> FEATURE:
<223> OTHER INFORMATION: RAS(23351)D RD-PCR primer

<400> SEQUENCE: 6
agtggccatt tgtccgtcat                                             20

<210> SEQ ID NO 7
<211> LENGTH: 20
<212> TYPE: DNA
<213> ORGANISM: Artificial Sequence
<220> FEATURE:
<223> OTHER INFORMATION: RAS(23768)U RD-PCR primer

<400> SEQUENCE: 7
gcatggcatt agcaaagact                                             20

<210> SEQ ID NO 8
<211> LENGTH: 10
<212> TYPE: DNA
<213> ORGANISM: Artificial Sequence
<220> FEATURE:
<223> OTHER INFORMATION: 10-nucleotide universal tail for KRAS primers

<400> SEQUENCE: 8
ggccaagtga                                                        10

<210> SEQ ID NO 9
<211> LENGTH: 22
<212> TYPE: DNA
<213> ORGANISM: Artificial Sequence
<220> FEATURE:
<223> OTHER INFORMATION: Exon 2 forward primer

<400> SEQUENCE: 9
ctggtggagt atttgatagt gt                                          22

<210> SEQ ID NO 10
<211> LENGTH: 21
<212> TYPE: DNA
<213> ORGANISM: Artificial Sequence
<220> FEATURE:
<223> OTHER INFORMATION: Exon 2 reverse primer
```

```
<400> SEQUENCE: 10
actcccaagg aaagtaaagt t                                              21
```